(12) United States Patent
Turner et al.

(10) Patent No.: US 8,088,077 B2
(45) Date of Patent: Jan. 3, 2012

(54) TINNITUS TESTING DEVICE AND METHOD

(75) Inventors: Jeremy Turner, Jacksonville, IL (US); James Michael Kinder, Julian, CA (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 1330 days.

(21) Appl. No.: 11/669,767

(22) Filed: Jan. 31, 2007

(65) Prior Publication Data

US 2007/0270920 A1    Nov. 22, 2007

Related U.S. Application Data

(60) Provisional application No. 60/835,162, filed on Aug. 2, 2006, provisional application No. 60/801,229, filed on May 16, 2006.

(51) Int. Cl.
*A61B 5/00* (2006.01)
*A61B 5/04* (2006.01)

(52) U.S. Cl. .................. 600/559; 600/544

(58) Field of Classification Search .............. 600/559, 600/25, 28, 544–545; 607/55–56
See application file for complete search history.

(56) References Cited

U.S. PATENT DOCUMENTS

| | | | |
|---|---|---|---|
| 3,949,735 A | 4/1976 | Klar et al. | |
| 4,201,225 A | 5/1980 | Bethea, III et al. | |
| 5,143,081 A | 9/1992 | Young et al. | |
| 5,795,287 A * | 8/1998 | Ball et al. | 600/25 |
| 5,868,683 A | 2/1999 | Protopapas et al. | |
| 6,155,971 A | 12/2000 | Calhoun et al. | |
| 6,602,202 B2 | 8/2003 | John et al. | |
| 6,631,295 B2 | 10/2003 | Rubinstein et al. | |
| 6,682,472 B1 | 1/2004 | Davis | |
| 6,687,525 B2 | 2/2004 | Llinas et al. | |
| 7,014,613 B2 | 3/2006 | John et al. | |
| 2001/0049480 A1 | 12/2001 | John et al. | |
| 2002/0055675 A1 | 5/2002 | Llinas et al. | |
| 2002/0091423 A1 | 7/2002 | Rubinstein et al. | |
| 2002/0173697 A1 * | 11/2002 | Lenhardt | 600/25 |
| 2003/0100998 A2 * | 5/2003 | Brunner et al. | 702/19 |
| 2003/0114728 A1 * | 6/2003 | Choy | 600/28 |
| 2003/0149553 A1 | 8/2003 | Holzrichter | |
| 2004/0064066 A1 | 4/2004 | John et al. | |
| 2004/0127812 A1 | 7/2004 | Micheyl et al. | |

(Continued)

FOREIGN PATENT DOCUMENTS

CN    1090159    8/1994

(Continued)

OTHER PUBLICATIONS

Turner et al, Gap Detection Deficits in Rats with Tinnitus: A Potential Novel Screening Tool, Feb. 2006, Behavioral Neuroscience 2006, vol. 120, No. 1, p. 188-195.*

(Continued)

*Primary Examiner* — Max Hindenburg
*Assistant Examiner* — Huong Q. Nguyen
(74) *Attorney, Agent, or Firm* — Senniger Powers LLP

(57) ABSTRACT

Objectively measuring tinnitus in human and animal subjects. A subject is exposed to an alteration in a sound pattern otherwise qualitatively similar to the subject's tinnitus and a startle reflex is induced. The subject's acoustic startle response is obtained and used to determine whether the subject detected the alteration of the sound pattern.

23 Claims, 16 Drawing Sheets

U.S. PATENT DOCUMENTS

| | | | |
|---|---|---|---|
| 2004/0204659 A1 | 10/2004 | John et al. | |
| 2005/0013445 A1 | 1/2005 | Martin | |
| 2005/0043646 A1 | 2/2005 | Viirre et al. | |
| 2005/0070812 A1 | 3/2005 | Donofrio | |
| 2005/0273017 A1* | 12/2005 | Gordon | 600/544 |
| 2006/0020161 A1 | 1/2006 | Mageras et al. | |
| 2006/0093997 A1 | 5/2006 | Kearby et al. | |
| 2006/0167335 A1 | 7/2006 | Park et al. | |
| 2009/0099476 A1 | 4/2009 | Fogel et al. | |

FOREIGN PATENT DOCUMENTS

| | | |
|---|---|---|
| CN | 1663528 | 9/2005 |
| WO | 0242986 A1 | 5/2002 |
| WO | 0247547 A1 | 6/2002 |
| WO | 03026478 A1 | 4/2003 |

OTHER PUBLICATIONS

Barsz et al., "Behavioral and neural measures of auditory temporal acuity in aging humans and mice", Neurobiology of Aging 23 (2002) 565-578.

Glasberg et al., "Gap detection and masking in hearing-impaired and normal-hearing subjects", J. Acoust. Soc. Am., vol. 81, No. 5, May 1987, pp. 1546-1556.

Ison et al., "The behavioral response of mice to gaps in noise depends on its spectral components and its bandwidth", J. Acoust. Soc. Am., vol. 117, No. 6, Jun. 2005, pp. 3944-3951.

Ison, "Temporal Acuity in Auditory Function in the Rat: Reflex Inhibition by Brief Gaps in Noise", Copyright 1982 by the American Psychological Association, Inc., pp. 945-954.

Turner, Jeremy, et al., "Behavioral Gap Detection Deficits in the Fischer Brown Norway (FBN) Rat Model of Presbycusis", Abstract 206, Session J11:Aging: Animal Studies, Feb. 21, 2005.

Brozoski, Thomas, et al., Patterns of Cochlear Pathology, Neural Activity in the Inferior Colliculus, and Psychophysical Evidence of Tinnitus in Chinchillas, Abstract 709, Session T8: Inner Ear Anatomy and Physiology 3 Feb. 23, 2005.

Nagler, Stephen M., MD, "Masking in the Millennium," available at URL: http://tinn.com/ citing Tinnitus Today, Journal of the American Tinnitus Association, downloaded on Apr. 17, 2006, 2 pages.

"Tinnitus," American Academy of Otolaryngology—Head and Neck Surgery, available at URL: http://www.entnet.org/healthinfo/hearing/tinnitus.cfm, downloaded on Apr. 17, 2006, 4 pages.

"Tinnitus," American Speech-Language-Hearing Association, available at URL: http://www.asha.org/public/hearing/disorders/Tinnitus.htm, downloaded on Apr. 17, 2006, 3 pages.

Formby, C., Sherlock, L. P. & LI, S., Temporal gap detection measured with multiple sinusoidal markers: Effects of marker number, frequency and temporal position, J. Acoust. Soc. Am., 104, 1998, pp. 984-998.

Formby, C., Gerber, M. J., Sherlock, L. P. & Magder, L. S., Evidence for an across-frequency two-channel process in asymptotic monaural temporal gap detection, J. Acoust. Soc. Am., 103, 1998, pp. 3554-3560.

Forrest, T. G., Formby, C. & Sherlock, L. P., Measurement and modeling of temporal gap detection for normal and Meniere listeners, 1997, pp. 373-386 in W. Jesteadt (Ed.), Modeling Sensorineural Hearing Loss, Mahway, NJ: Erlbaum Inc.

Parsons et al., Correlating behavioural evidence of tinnitus and auditory cortex plasticity in the rat, Abstract A180.13, published in FENS Forum Abstracts, vol. 3, 2006, Ref.: FENS Abstr., vol. 3, A180.13, 2006,; found at http://fens2006.neurosciences.asso.fr/abstracts/R6/A180_13.html.

Keith, Robert, W., Ph.D., "Gap detection", Jan. 27, 2003, http://www.audiologyonline.com/askexpert/display_question.asp?question_id=154.

Turner, Jeremy, T., et al., Gap Detection Deficits in Rats with Tinnitus: A Potential Novel Screening Tool, Behavioral Neuroscience, Feb. 27, 2006, 188-195, vol. 120, No. 1, American Psychological Association, USA.

Turner, J.G., Gap Detection As a High Throughput, Objective Behavioral Screen for Tinnitus, 2006, http://www.tinnitusresearch.org/en/meetings/files2006/Turner-abstract_for_poster-GAP_detection.pdf.

Elble, Rodger, J., M.D., & Moore, Curt, SIU School of Medicine, Department of Neurology Newsletter, Mar. 2006, 2 pages, vol. 2.

Turner, Jeremy, G., et al., Abstract: Novel Technique for Rapid Screening of Tinnitus in Rats, Acoustical Society of America Journal, published Apr. 2005, pp. 2468-2468, vol. 117, Issue 4, ASAJ Homepage, American Institute of Physics, USA.

Willot et al., "Neural Plasticity in the Mouse Inferior Colliculus: Relationship to Hearing Loss, Augmented Acoustic Stimulation, and Prepulse Inhibition," Hearing Research, Sep. 2000, vol. 147, issues 1-2, pp. 275-281.

* cited by examiner

200

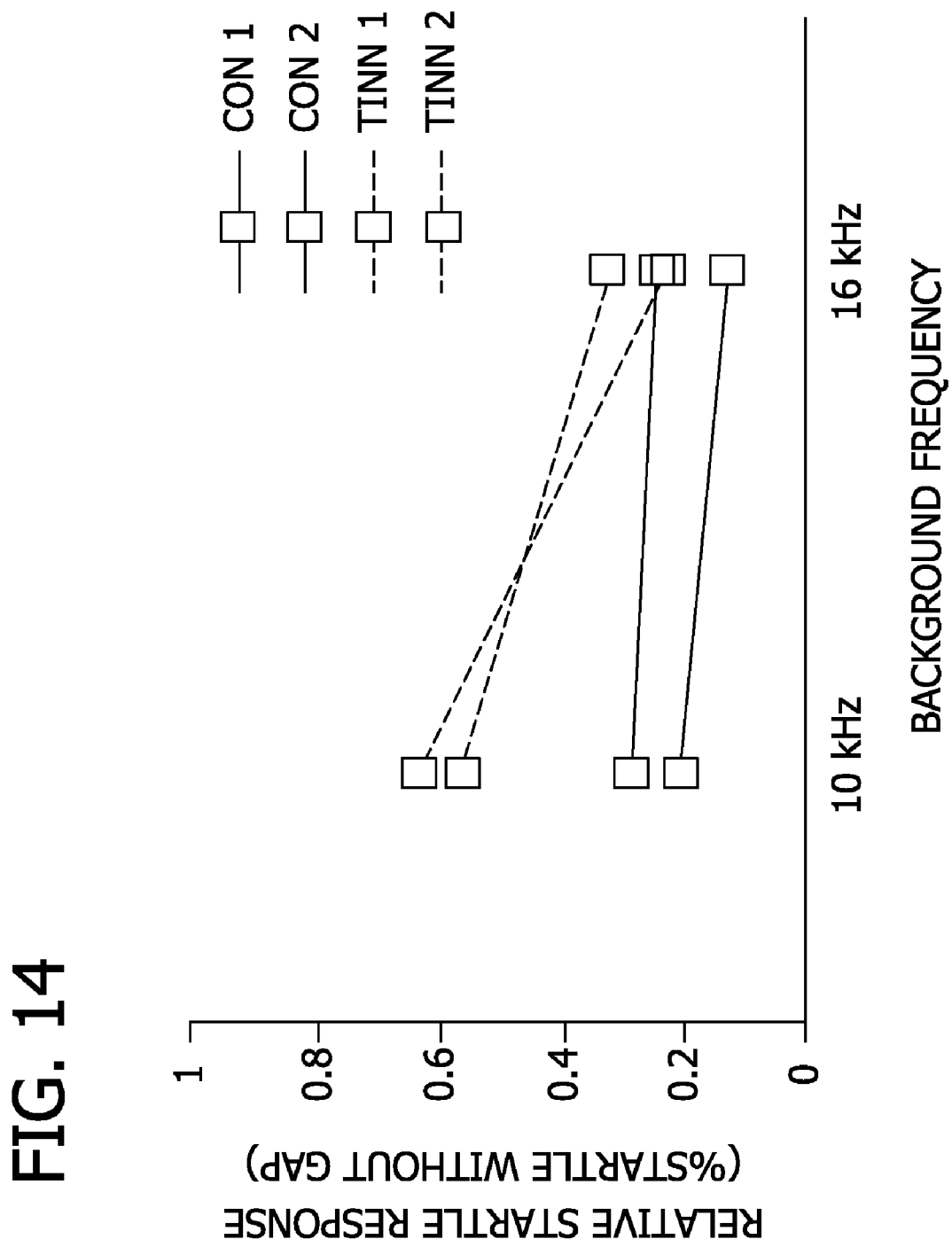

TINNITUS TESTING DEVICE AND METHOD

CROSS-REFERENCE TO RELATED APPLICATION

This application claims the benefit of U.S. Provisional Patent Application No. 60/835,162, filed Aug. 2, 2006, the entire disclosure of which is incorporated herein by reference. This application additionally claims the benefit of U.S. Provisional Patent Application No. 60/801,229 filed May 16, 2006, the entire disclosure of which is incorporated herein by reference.

STATEMENT OF GOVERNMENT INTEREST

This invention was made with government support under grant number AG023910 awarded by the National Institutes of Health. The government has certain rights in the invention.

BACKGROUND

Tinnitus is the perception of noise in the ears or head when no external sound is present. It is sometimes referred to as ringing in the ears, but people report hearing all kinds of sounds such as cricket chirps, whooshing, hissing, pulsing, and buzzing. It can vary in pitch from a low roar to a high squeal or whine, and may be heard in one or both ears. When the ringing is fairly constant, it can be annoying and distracting. As many as 50 million Americans suffer from tinnitus in some form. More than seven million people suffer severe and disabling symptoms significantly impacting their quality of life. Because tinnitus is associated with aging, and human longevity is increasing, the impact of tinnitus on society will likely get worse.

Despite the prevalence of tinnitus and its debilitating symptoms in many patients, the cause(s) of tinnitus imperative to precise prevention and treatment remain largely unknown. Currently, causes(s) and treatment(s) of tinnitus are especially difficult to identify because conventional testing techniques are unable to accurately and reliably detect and quantify tinnitus. One common detection and characterization method involves exposing a subject to several different sound patterns and asking the subject which sound pattern is the most qualitatively similar to the sounds he or she perceives. While this method is beneficial for detecting tinnitus in some subjects, it is not effective where the subject is unable to communicate with the test administrator or where the subject cannot perceive all of the effects of the subject's own tinnitus condition. Because this approach relies solely on the subject to explain his or her symptoms, this approach is also subject to malingering; a condition where a subject claims to have a medical problem, such as tinnitus, when such problem does not actually exist. There are many reasons for malingering related to tinnitus, one of which includes fraudulently collecting disability reimbursement. Currently, such fraud is a particular issue concerning military disability reimbursement. Another reason for malingering relates to psychiatric disorders suffered by subjects. A subject may believe he or she experiences tinnitus because he or she perceives sounds as a result of a psychiatric disorder when, in fact, no tinnitus actually exists.

In other cases, the subjects are animals and cannot reliably communicate with the test administrator. Animal models have been developed and used in an effort to improve detection techniques and prevention and treatment measures for tinnitus. Tinnitus may be modeled in animals by inducing a peripheral hearing loss, such as a loud sound exposure, which is a known cause of tinnitus in humans and performing behavioral tests to provide indicators of an animal's tinnitus. These behavioral tests require training animals to respond distinctively to the presence or absence of an acoustic stimulus. In some of these models, tinnitus is indicated when no external sound is present and the animals respond distinctively indicating that the animals hear sound. Because the behavioral training is based on the animals' ability to learn, remember, and voluntarily communicate with the test administrator, such animal models have inherent accuracy and implementation issues. In addition, the animal models typically require complex behavior manipulations (e.g., food or water deprivation, finely tuned shock parameters, variable reinforcement schedules) and weeks to months of complicated behavioral training. Thus, due to the subjective nature of tinnitus in both humans and laboratory animals, tinnitus testing techniques relying on the subjective response of the subject are generally problematic.

Similarly, current detection techniques relating to an objective response of the subject are insufficient to accurately and reliably detect and measure tinnitus. One objective detection method discussed in PCT application WO/02/47547 determines the presence of tinnitus by detecting the presence of pain. The method measures the electrical output of nerve fibers, which is associated with pain. However, such a method may not be appropriate for subjects experiencing pain from sources other than tinnitus. Moreover, this method describes determining the presence of tinnitus in a subject; it does not describe a method of objectively quantifying or determining the severity of the subject's tinnitus. The ability to quantify a subject's tinnitus is crucial to finding a proper and suitable treatment for a subject's tinnitus.

Objective methods of detecting other disorders having subjective symptoms, such as schizophrenia, include pre-pulse inhibition deficit testing. Schizophrenia has been associated with abnormalities in information processing, sometimes referred to as sensory gating failures. Gating generally allows for the screening or filtering of unimportant stimuli in order to respond and process important stimuli and related information. Sensory gating failures of subjects have been evaluated by analyzing the subject's pre-pulse inhibition deficit. All mammals respond to sudden intense stimuli (reflex stimulus) in modalities that consist of a series of flexion and extension responses (startle response). In humans, startle reflex magnitude diminishes when a weak pre-pulse stimulus precedes the reflex stimulus. Although identifying pre-pulse inhibition deficits has been advantageous in the detection of sensory gating failures related to schizophrenia, comparable tests for detecting the perception of sounds related to tinnitus have not been developed.

Thus, a need exists, in the testing of both human and animal subjects, for a method and apparatus to objectively measure tinnitus.

SUMMARY

Embodiments of the present invention overcome one or more deficiencies of conventional practices related to detecting tinnitus by analyzing a subject's acoustic startle reflex. In addition, embodiments of the invention advantageously objectively measure the severity of the subject's tinnitus based on the subject's startle response to various selected sound patterns which each include a reflex stimulus.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

FIG. 14 is a graph illustrating gap detection performance in tinnitus subjects and in control subjects, said tinnitus and control subjects having no training using the Bauer and Brozoski operant method, according to an embodiment of the invention described in Appendices A and B.

Corresponding reference characters indicate corresponding parts throughout the drawings.

DETAILED DESCRIPTION

Figure 1A:
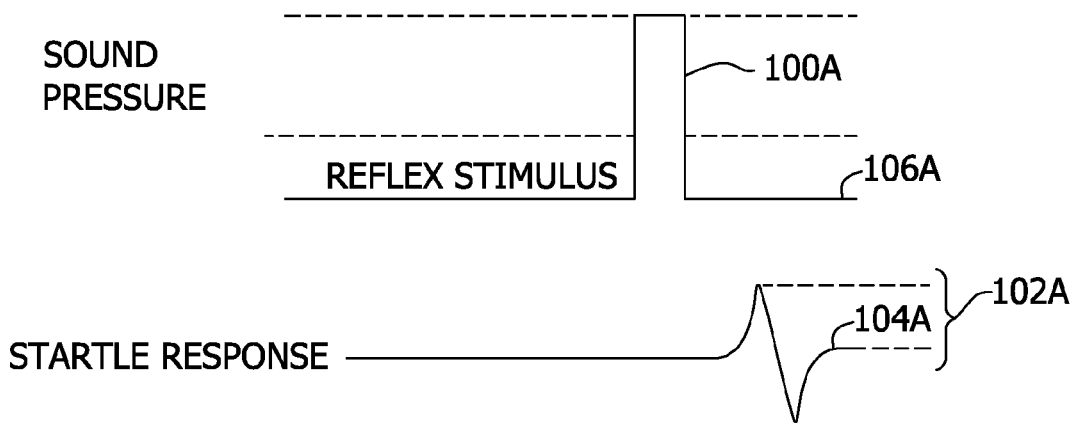
FIG. 1A is graph illustrating a subject's acoustic startle reflex, wherein said subject does not have tinnitus.
Figure 1B:
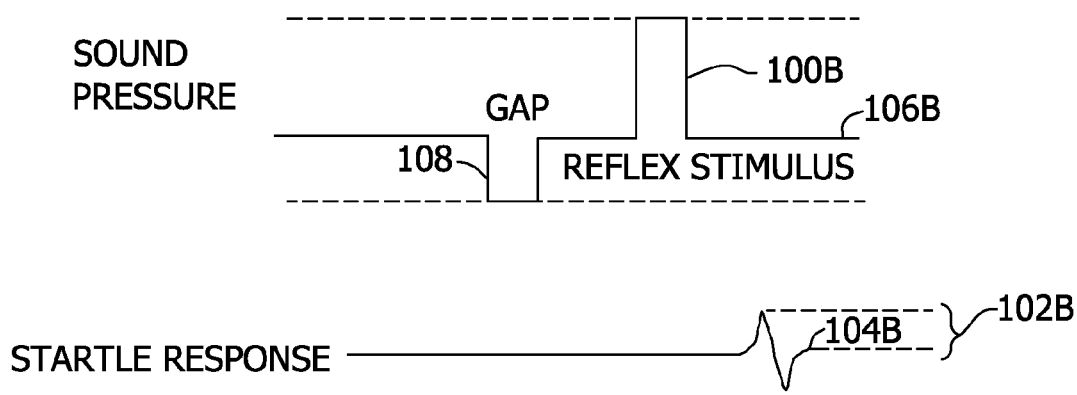
FIG. 1B is a graph illustrating a subject's startle pre-pulse inhibition, wherein said subject does not have tinnitus.
Figure 1C:
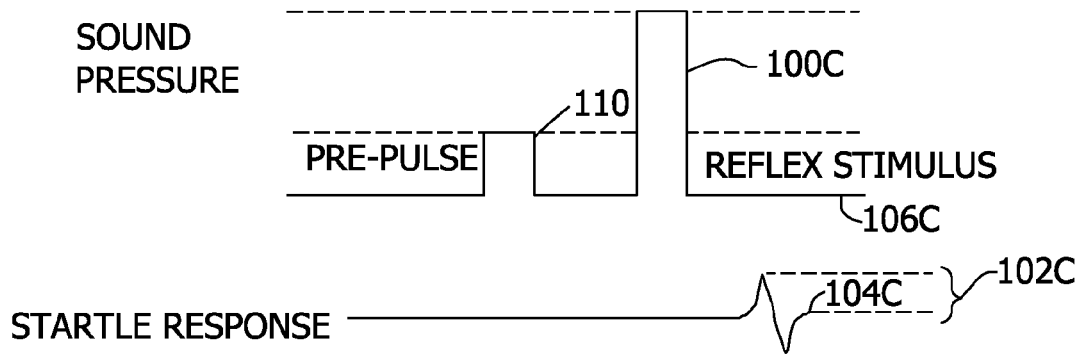
FIG. 1C is a graph illustrating a subject's gap inhibition, wherein said subject does not have tinnitus.

Embodiments of the invention effectively detect and quantify tinnitus of a human or animal subject by analyzing the subject's acoustic startle reflex (startle). Referring to FIG. 1A, the acoustic startle reflex, present in animals and humans, is a response (startle response) 104A in the form of a sudden movement to a stimulus (reflex stimulus) in the form of, for example, an unexpected loud noise 100A. Particularly, embodiments of the present invention objectively measure a subject's tinnitus by quantifying the subject's startle response and applying the magnitude of the startle response to analyze the subject's gap inhibition and pre-pulse inhibition. Gap inhibition, illustrated in FIG. 1B, refers to the inhibition of the subject's acoustic startle reflex (e.g., compare startle response 104A to startle response 104B) due to exposure to a gap 108 in an otherwise constant background acoustic signal 106B preceding the subject's exposure to a reflex stimulus 100B. Pre-pulse inhibition, illustrated in FIG. 1C, refers to the inhibition of the subject's acoustic startle reflex (e.g., compare startle response 104A to startle response 104C) due to exposing the subject to a weak pre-pulse 110 over an otherwise constant background acoustic signal 106C preceding the subject's exposure to a reflex stimulus 100C. According to aspects of the present invention, a subject's tinnitus prevents the subject from detecting the gap of sound and, thus, the subject's acoustic startle reflex will not be inhibited when the reflex stimulus is preceded by a gap of sound as would occur in a subject (e.g., as illustrated in FIG. 1B) without tinnitus. According to other aspects of the present invention, a subject's ability to detect a plurality of pre-pulses having different sound patterns is a function of the subject's tinnitus, and, thus, the subject's acoustic startle reflex will be inhibited as a function of the subject's tinnitus. Advantageously, exemplary embodiments of the present invention improve the detection and objective measurement of tinnitus by testing the subject's startle response.

Figure 2:
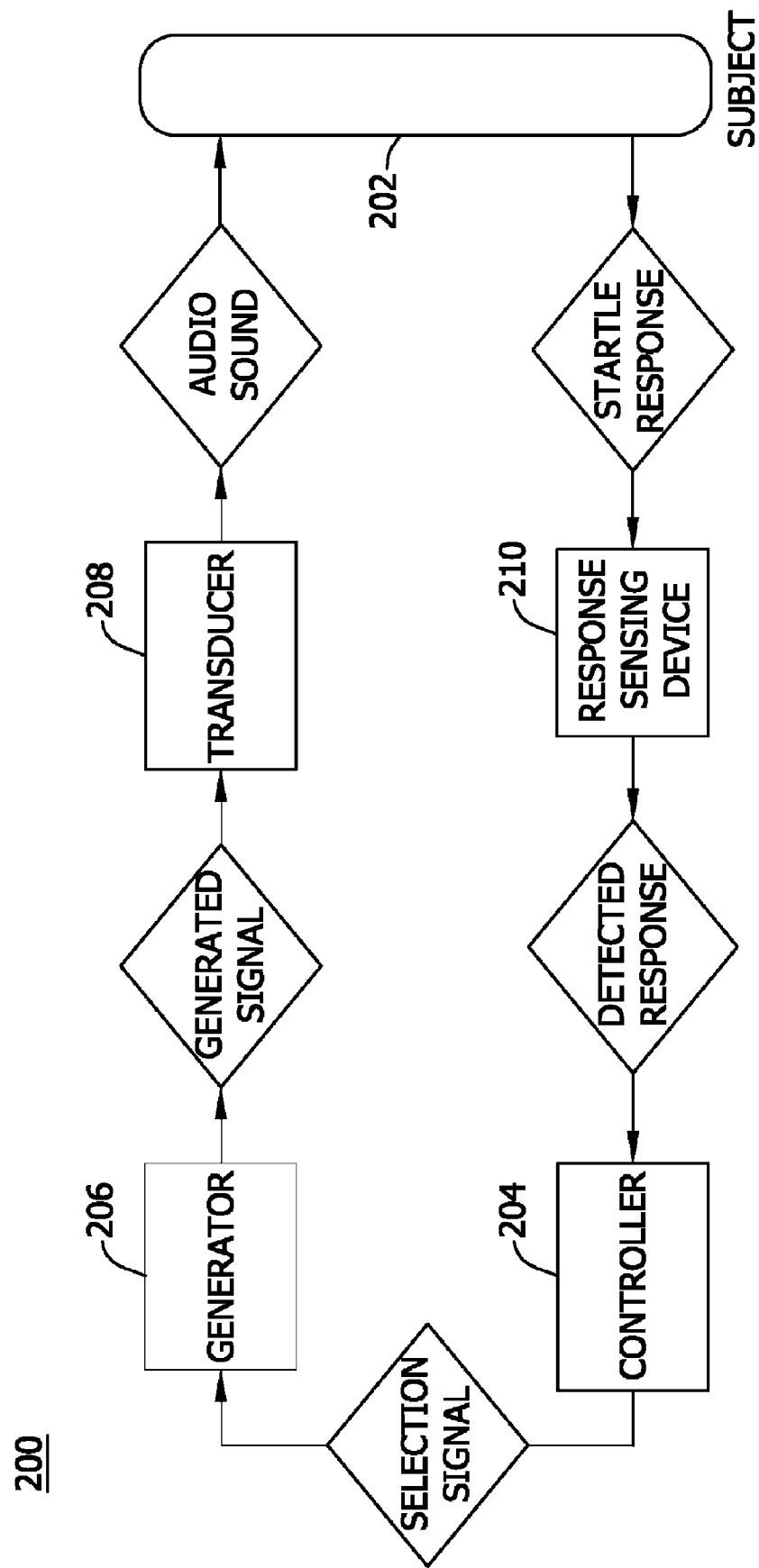
FIG. 2 is flow diagram illustrating a device for objectively measuring a subject's tinnitus according to an embodiment of the invention.

Referring to FIG. 2, a device 200 for objectively measuring tinnitus of a human or animal subject 202 embodying aspects of the present invention is illustrated. In general, the device includes a controller 204, a generator 206, a transducer 208, and a response sensing device 210. In one embodiment of the device 200, the controller 204 selects sound patterns to be exposed to the subject. The generator 206 generates signals associated with the sound patterns selected by the controller 204, and the transducer 208 converts the generated signals to the selected sound patterns. The device 200 exposes the selected sound patterns to the subject 202 via the transducer 208. In turn, the response sensing device 210 obtains the subject's startle response to the sound patterns produced by the transducer 208 and the controller 204 uses the obtained startle response to measure the subject's tinnitus or lack thereof. As described in detail below, the sound patterns may be selected to qualitatively approximate or contrast the sound heard by the subject due to the subject's tinnitus. In this manner, embodiments of the invention permit measuring the subject's tinnitus as a function of an elicited startle response.

Figure 3:
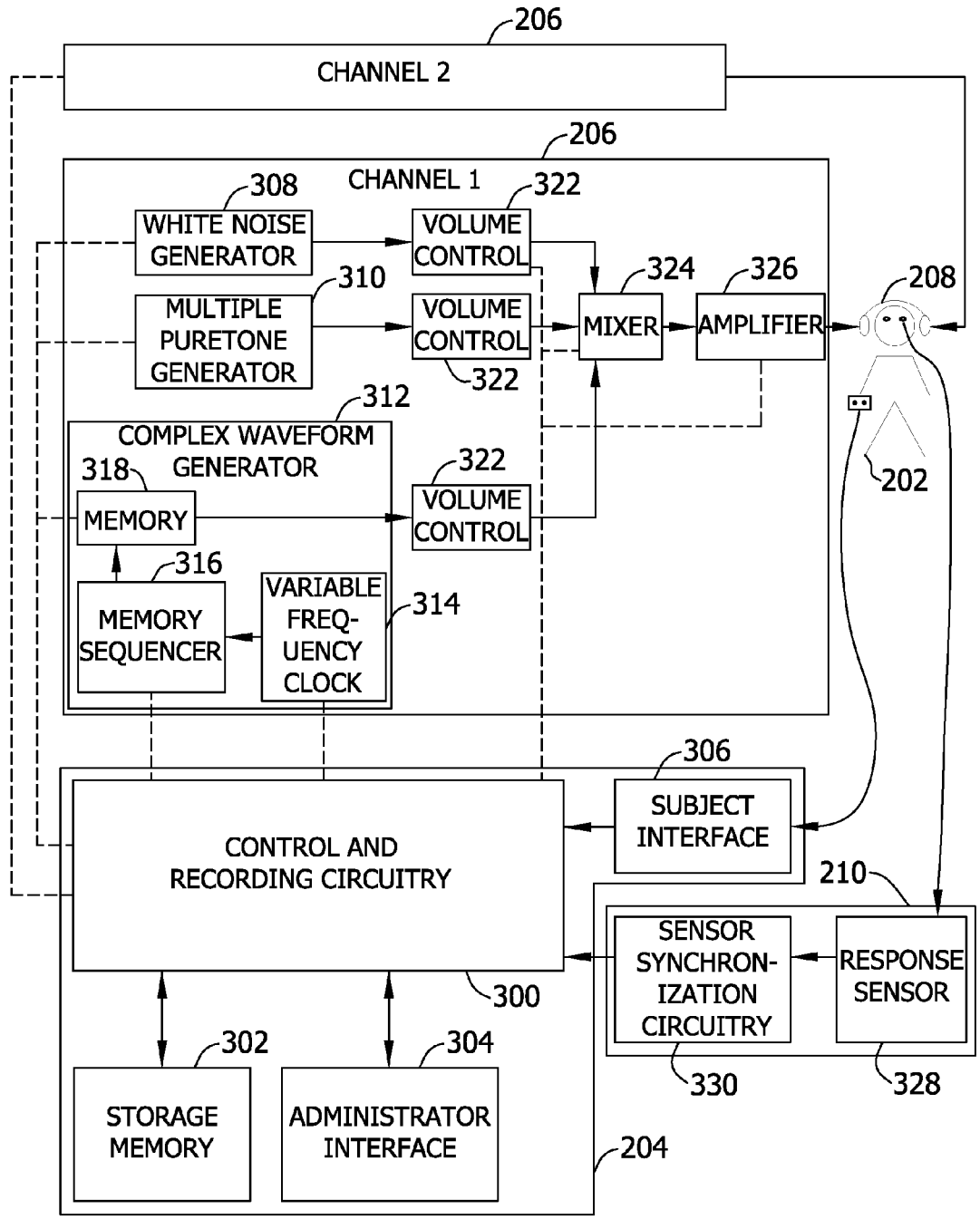
FIG. 3 is block diagram illustrating a device for objectively measuring a subject's tinnitus, according to an embodiment of the invention.

As shown in FIG. 3, the controller 204 comprises circuitry for selecting sound patterns, recording obtained startle responses, and analyzing the recorded startle responses. In one embodiment, a control and recording circuit 300, such as a computing device, controls the selection and generating of sound patterns and records the resultant startle response data. Exemplary computing devices include one or a combination of the following: a personal computer (PC), a workstation, a portable digital device, a personal digital assistance (PDA), a pocket PC, and various other digital devices known in the art. As is known to those skilled in the art, computing devices include a combination of the following (not shown): a processing unit, one or more computer-readable storage media, an internal bus system coupling to various components within the computing devices, Input/Output devices, a networking device, and other devices. In one alternative embodiment, the control and recording circuitry 300 is a control system including a microcontroller and/or a programmable logic controller.

The controller 204 further comprises a storage memory 302 for storing data including: data used by the control and recording circuit 300 to select sound patterns, startle response data recorded by the control and recording circuit 300, and data used by the control and recording circuit 300 to analyze recorded startle response data. As is known in the art, control and recording circuit 300 and the storage memory 302 communicate data therebetween via a wired or wireless connection coupling the controller 204 components. In one embodiment, the storage memory 302 is included in the control and recording circuit 300 in the form of volatile and/or non-volatile memory. Internal exemplary storage media include RAM, ROM, EEPROM, flash memory and/or other internal storage media known in the art. In another embodiment, the storage memory 302 is external to the control and recording circuitry 300. Exemplary external storage media include memory sticks, CD-ROM, digital versatile disks (DVD), magnetic cassettes, magnetic tape, magnetic disks and/or other storage media known in the art.

In one embodiment, controller 204 further comprises an administrator interface 304 for communicating with a testing administrator and/or a subject interface 306 for communicating with the subject. These communications include the control and recording circuit 300 data, the data stored in the storage memory 302 for selecting sound patterns, and the like.

Using the interface 304, a testing administrator initiates, for example, the selection of a sound pattern for presentation to the subject under test. The control and recording circuit 300 responds using data (e.g., program, instructions) stored in the storage memory 302, which prompt the testing administrator to provide data related to selecting a sound pattern, such as the desired type of sound, volume, duration, and amplitude. The testing administrator provides the information via the interface 304 and control and recording circuit 300 selects the sound pattern according to the provided information. The subject responds to his or her exposure to the selected sound pattern via the subject interface 306 and provides similar information which is used for selecting a second sound pattern based on his perception of the first sound pattern. The control and recording device 300 delivers the information provided by the subject to the testing administrator via the administrator interface 304.

According to embodiments of the invention, the administrator interface 304 may be an input and an output device, including a keyboard and a monitor, and the subject interface 306 is an input device, including a keyboard. In other embodiments, the administrator interface 304 and/or the subject interface 306 include one or more of the following input devices: keyboard, mouse, trackball, pen, touch pad, microphone, joystick, gamepad, push button, touch screen, and other input devices known in the art. Additionally, the administrator interface 304 and/or the subject interface 306 include one or more of the following output devices: monitor, printer, speakers, lights and other output devices known in the art.

The control and recording circuit 300 communicates a signal to the generator 206 indicating a selected sound pattern. Upon receiving the signal indicating the selected pattern from the control and recording circuit 300, the generator generates a signal associated with the selected sound pattern. In one embodiment, the selected sound pattern includes a background acoustic signal, a gap in the background acoustic signal, and/or a reflex stimulus signal. The background acoustic signal has acoustic characteristics (e.g., amplitude, wavelength, pattern, frequency, speed, duration, volume, and other related characteristics) such that the background acoustic signal mimics tinnitus sounds (e.g., whooshing, hissing, pulsing, buzzing, pure tone). The gap in the background acoustic signal includes removing or lowering the background acoustic signal so that it is not audible. The reflex stimulus includes a signal such as white noise or a pure tone known in the art to generally elicit an acoustic startle reflex in humans where the subject is a human and likewise in animals where the subject is an animal. In another embodiment, the selected sound pattern includes the background acoustic signal, a test acoustic signal, and/or the reflex stimulus signal. The test signal has acoustic characteristics (e.g., amplitude, wavelength, frequency, speed, duration, volume, and other related characteristics), at least one of which is different from the background signal. For example, the test signal has volume which is greater than the volume of the background signal but otherwise has acoustic characteristics identical to those of the background signal. In another example, each and every acoustic characteristic of the test signal is different from each and every acoustic characteristic of the background signal. In yet another example, the acoustic characteristics of the test signal are limited such that the test signal does not elicit a startle response from the subject.

Referring further to FIG. 3, the generator 206 comprises one or more electronic signal generators 308, 310, 312, a volume control 322, a sound mixer 324, and an amplifier 326. A wired or wireless connection couples the electronic signal generators 308, 310, 312 to corresponding volume controls 322; the corresponding volume controls 322 to the sound mixer 324; and the sound mixer 324 to the amplifier 326. The electronic signal generators include, for example, a white noise generator 308 and a multiple pure tone generator 310 for generating sound wave signals associated with a reflex stimulus signal and/or a test signal, and a complex waveform generator 312 for generating sound wave signals associated with a background signal and/or a test signal. In alternative embodiments, alternative or additional electronic signal generators known in the art are used. The electronic generators transmit generated sound wave signals to the corresponding volume controls 322. The volume controls 322 associate a volume with the generated sound wave signals. The volume controls 332 transmit generated sound waves signals with volume to the sound mixer 324. The sound mixer 324 receives sound wave signals generated from any of the electronic signal generators and provides the amplifier 326 with the generated wave signal and volume associated with the selected sound pattern or a portion thereof In an embodiment, the wave signal associated with the selected sound pattern is a combination of wave signals generated from multiple electronic signal generators. The sound mixer 324 combines the generated wave signals and provides the amplifier 326 with a combined wave signal associated with the selected sound pattern. The amplifier 326 boosts the wave signal provided by the sound mixer 324 based on the volume associated with the selected sound pattern. In alternative embodiments, the generator 206 comprises any device generating sound such as a device comprising a memory or utilizing the storage memory 302 for digitally storing sound patterns (e.g., .wav files) for selecting, a digital signal processor for converting the digitally stored sound patterns to sound waves signals, and an amplifier 206 for boosting the sound wave signals.

In one embodiment, the control and recording circuit 300 is coupled to each of the electronic signal generators via a wired or wireless connection. The control and recording circuit 300 selects a sound pattern by sending a signal to one or more of the electronic signal generators which generates sound wave signals associated with the selected sound pattern. For example, the control and recording circuit 300 selects a reflex stimulus having a white noise waveform to the white noise generator 308. Similarly, the control and recording circuit 300 selects a reflex stimulus having a particular pure tone waveform by sending a signal to the multiple pure tone generator 310 indicating the particular pure tone. In one embodiment, the electronic signal generators include a memory for storing data defining sound wave signals associated with particular sound patterns and the electronic signal generator uses the stored data to generate the sound wave signal when a particular sound pattern is selected by the control and recording circuit 300. For example, the complex waveform generator includes a memory 318 for storing a plurality of waveforms associated with the various background acoustic signals (e.g., whooshing, hissing, pulsing, buzzing, pure tone). The control and recording circuit 300 selects a background acoustic signal (e.g., hissing) by sending a signal to the memory 318 to retrieve and generate the waveform stored in the memory 318 that is associated with the selected (e.g., hissing) background sound. In one embodiment, the electronic signal generators include a component allowing the control and recording circuit 300 to link and/or modify the waveforms stored in the memory and to generate the resulting waveform. For example, the complex waveform generator includes a variable frequency clock 314 and a memory sequencer 316 for linking and modifying waveforms stored in the memory. The control and recording circuit 300 selects a background acoustic signal which does not exist in the memory 318 (e.g., fast pulse alternating with hissing) by sending a signal to the memory 318 to retrieve stored waveform(s) (e.g., waveform associated with pulsing and waveform associated with hissing). The control and recording circuit 300 also sends signals to the variable frequency clock 314 and the memory sequencer 316 to modify the frequency of the pulse waveform and link it with the hissing waveform.

In one embodiment, the control and recording circuit 300 is further coupled to the volume controls 322, the sound mixer 324, and the amplifier 326 via a wired or wireless connection. In one embodiment, the control and recording circuit 300 sends a signal to the volume control 322 to indicate the volume associated with the selected sound pattern. Similarly, the control and recording circuit 300 sends a signal to the sound mixer 324 for indicating the electronic wave generator 308, 310, or 312 of the wave signal associated with the selected sound pattern. The control and recording circuit 300 sends a signal to the amplifier 326 indicating the amplitude and duration wave signal associated with the selected sound pattern.

The amplifier 326 is further coupled to the transducer 208 as shown in FIG. 3. The transducer 208 receives the wave signal associated with the selected sound pattern and converts the wave signal to the selected sound pattern for exposing to the subject 202. The transducer 208 can be any device, such as a speaker, known in the art for converting a wave signal to a sound pattern. In one embodiment, the transducer 208 may be incorporated into a device(s), such as headphones, for exposing the sound pattern to the subject. The device may include component(s) to prevent the subject from hearing any sounds other than the sounds provided by the transducer 208. In one embodiment, the device includes multiple generators 206 and corresponding transducers 208. For example two generators 206 may be used to generate two different sound waves and two transducers 208 are used to convert each of the sound waves generated by each generator 206 to a sound pattern. The transducers 208 may be incorporated into headphones for exposing the sound waves to each of the subject's ears.

The response sensing device 210 is associated with the subject 202 for detecting the subject's startle response to the sound pattern. The response sensing device 210 comprises a response sensor 328 and sensor synchronization circuitry 330. The response sensor 328 and the sensor synchronization circuitry 330 are coupled via a wired or wireless connection. In one embodiment, the response sensing device 210 detects the subject's startle response to the sound pattern by monitoring the subject's eyelid movement and/or movement of muscles associated with eyelid movement. The startle reflex in humans is a relatively simple behavioral reflex consisting of a rapid blink of the eyes (mediated by the obicularis oculi muscles) that can be easily measured by a variety of methods. For example, a mechanical lever is attached to one of the subject's eyelids and the response sensor 328 (e.g., Hall effect sensor) communicates a signal to the synchronization circuitry 330 indicating movement of the lever/eyelids. In another example, an infra-red (IR) illuminator illuminates the eye, and the response sensor 328 detects the reflected light. During eyelid closure, more IR light is reflected to the response sensor 328 which is communicated (e.g., via an increase in voltage) to the synchronization circuitry 330. In yet another example, the response sensor 328 (e.g., electromyographic sensor) detects the electric potential generated by the muscles associated with the movement of the eyelid and communicates this movement to the synchronization circuitry 330. In another embodiment, the startle reflex is measured using the subject's brain waves associated with the startle reflex. For example, the response sensor 328 measures evoked potential changes in the subject's brain wave reflecting a response to the reflex stimulus. In yet another embodiment, particularly useful for animal subjects, the response sensing device 210 detects the subject's startle response to the sound pattern by monitoring the force associated with movement of the subject's leg muscles on a force sensing platform. When a startle inducing stimulus is presented, the rat engages in a reflexive series of muscle flexions and extensions in a variety of muscle groups (eyes, neck, legs, etc.), the sum of which is measured as force exerted to the floor. For example, the subject is placed on a floor and the general movement of the subject is confined. The response sensor 328 detects the force applied to the floor as a result of the subject's leg muscles and relays the data to the synchronization circuitry 330. The response sensing device 210 communicates the detected startle response to the control and recording circuit 300 and the control and recording circuit 300 measures the subject's tinnitus based on the detected startle response.

According to one embodiment, the device 200 is used to objectively measure the subject's tinnitus by testing the subject's gap inhibition. The device 200 tests the subject's gap inhibition by exposing the subject 202 a primary sound pattern having an audible gap in a background sound and then exposing the subject to a reflex stimulus. The audible gap is created in the primary sound pattern by exposing the subject to a background acoustic signal for a first duration and then removing/lowering the background acoustic signal for a second, shorter, duration. The background acoustic signal is selected to qualitatively match the subject's tinnitus. The characteristics of the background sound may be selected based on a number of factors, including the hearing range of the subject. For example, since the hearing range in humans is much lower in frequency than for rats, the frequency of background sounds is selected to have a different frequency for rat subjects than for human subjects. Particularly many humans describe their tinnitus as a high pitched hiss that sounds like a signal in the 3-8 kHz range. Thus, for human subjects, the background sound may consist of sounds with variable intensity and pattern having a frequency range of 250 Hz to 12,000 Hz. In contrast, for rat subjects, the frequencies presented may consist of band-pass filtered noise centered at various frequencies from 2-50 kHz (kilohertz).

The control and recording circuit 300 first selects the background acoustic signal which is qualitatively similar to the subject's tinnitus (e.g., hissing sound with a pressure of 65 decibels) by sending signals to the generator 206. Particularly, signals are sent to the complex waveform generator 312, the volume control 322, the sound mixer 324, and the amplifier 326 to select a wave signal having volume and amplitude associated with a hissing sound having a pressure of 65 decibels. The wave signal is converted to the selected background acoustic signal by the transducer 208 and exposed to the subject 202. Second, the control and recording circuit 300 selects an alteration of background acoustic signal for creating an audible gap (e.g., no sound, 0 decibels) in the background acoustic signal. The gap is selected by sending signals to the generator 206 indicating no sound wave is to be generated and the subject 202 is accordingly exposed to a gap/removal of the background acoustic signal. Alternatively, the control and recording circuit 300 selects the gap by sending signals to the volume control 322, the sound mixer 324, and/or the amplifier 326 to alter the wave signal associated with the background acoustic signal to have a pressure of 0 decibels for a short duration (e.g., 10-100 millisecond). Thus, the background acoustic signal is lowered for 10-100 millisecond so that it is exposed to the subject as a gap in the background pattern. Third, the control and recording circuit 300 sends a signal to the response sensing device 210 to begin monitoring the startle response of the subject. Fourth, the control and recording circuit 300 selects a reflex stimulus (e.g., white noise having a pressure of 110 decibels) by sending signals to the generator. Particularly, signals are sent to the white noise generator 308, the volume control 322, the sound mixer 324, and the amplifier 206 to select a wave signal having volume and amplitude associated with a white noise stimulus having a pressure of 110 decibels. The wave signal is converted to the selected background acoustic signal by the transducer 208 and exposed to the subject 202. The response sensing device 210 detects and the subject's startle response.

Figure 4A:
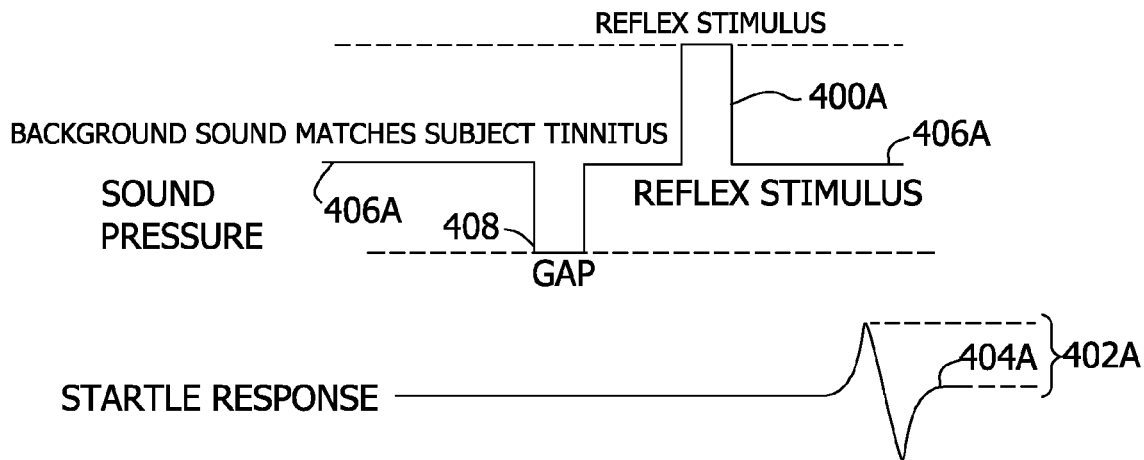
FIG. 4A is a graph illustrating a startle response of a subject elicited using gap inhibition testing techniques for measuring the subject's tinnitus, according to an embodiment of the invention.
Figure 4B:
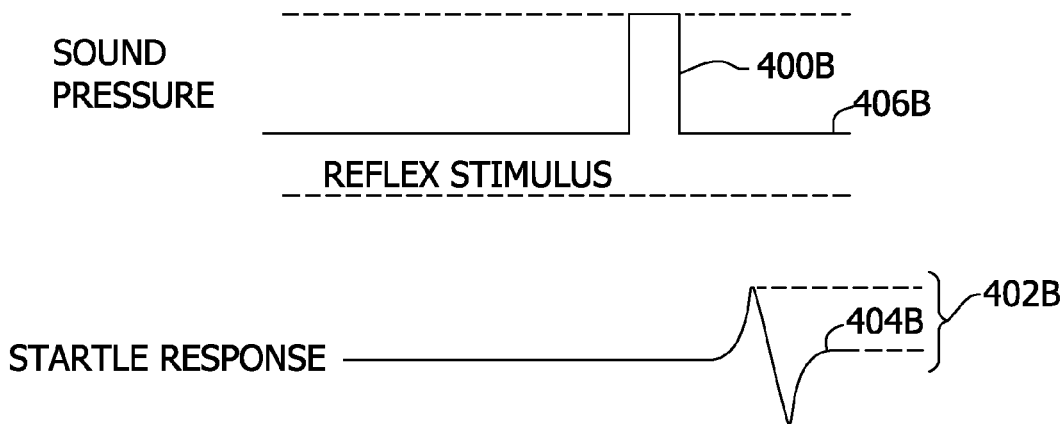
FIG. 4B is graph illustrating a startle response of a subject elicited by a reflex stimulus for measuring the subject's tinnitus according to an embodiment of the invention.

FIG. 4A illustrates the sound patterns exposed to the subject 202 and the subject's startle response. The sound patterns include the background acoustic signal 406A, the gap in the background acoustic signal 408, and the reflex stimulus signal 400A. The subject's startle response to the reflex stimulus 400A has an amplitude 402A. The amplitude 402A quantifies the subject's acoustic startle reflex. Specifically, since the subject's acoustic startle reflex is inhibited where the subject detects a gap in sound prior to the reflex stimulus, the amplitude of the subject's startle response will be less where the subject detects the gap in the background acoustic signal. Accordingly, the control and recording circuit 300 uses the amplitude 402A to determine whether the subject detected the gap 408 in the background acoustic signal 406A. Referring to FIGS. 4A and 4B, in one embodiment, the control and recording circuit 300 determines whether the subject detected the gap 408 in the background acoustic signal 406A by comparing (a) the amplitude 402A of the startle response 404A to a reflex stimulus 400A preceded by a gap 408; and (b) the amplitude 402B of a startle response to a reflex stimulus 400B not preceded by a gap. The latter startle amplitude 402B can be obtained using an embodiment of the present invention or by any method or device known in the art and then communicated to the control and recording circuit 300. The control and recording circuit 300 determines that the subject 202 detects the gap 408 in the background acoustic 406A if ratio of the amplitude 402A to the amplitude 402B is less than one. In this scenario, although the background acoustic signal was selected to substantially match the subject's perceived noise (tinnitus), the subject 202 was able to detect the absence of the background acoustic signal. Since the subject 202 was able to detect the absence of the background sound, the gap in sound did not inhibit the subject's acoustic startle reflex quantified by the amplitude of the startle response. Thus, the subject 202 does not have severe tinnitus. In an alternative embodiment, this scenario objectively indicates the background noise does match the subject's tinnitus. The control and recording circuit 300 determines that the subject 202 has not detected the gap 408 in the background acoustic signal 406A if the if ratio of the amplitude 402A to the amplitude 402B is equal to one. In this scenario, the subject 202 perceives a noise (tinnitus) substantially matching the background acoustic signal 406A so the subject 202 was unable to detect the presence or absence of the background acoustic signal 406A. Since the subject 202 was unable to detect the presence or absence of the background sound 406A, the gap 408 in sound did not inhibit the subject's acoustic startle reflex quantified by the amplitude 402A of the startle response. Thus, the subject 202 has tinnitus.

In addition to quantifiably and objectively measuring tinnitus in the subject, aspects of the present invention may be used to detect and qualitatively characterize tinnitus in the subject. For example, the test administrator can expose the subject to several different background acoustic signals. Particularly, by adjusting the intensity of the background sound from very quiet to relatively loud it would be possible to determine the sound pressure of the subject's tinnitus. For a very quiet tinnitus (e.g., 15 dB), presenting a silent gap in a moderately loud (e.g., 60 dB) background acoustic signal will not result in apparent deficits of the subject's startle reflex because the subject's tinnitus at 15 dB does not sufficiently fill the silent gap in the 60 dB background acoustic signal. If, however, the tinnitus is as loud as the background (60 dB) deficits of the subject's startle reflex will be quite apparent. Thus, in this example, the subject's startle response to the reflex stimulus will be the least inhibited when the background acoustic signal most closely approximates the existing sound perceived by the subject as a result of tinnitus.

According to one embodiment, the device 200 is used to objectively measure the subject's tinnitus by testing the subject's pre-pulse inhibition for a plurality of pre-pulse sounds. The device 200 tests the subject's pre-pulse inhibition by exposing the subject 202 a primary sound pattern comprising a background acoustic signal with a first duration and test acoustic signal having a shorter (e.g., pulse) second duration. The test acoustic signal is unique for each of the plurality of pre-pulse sounds but does not, in itself, elicit the subject's startle response. Particularly, the control and recording circuit 300 first selects a background acoustic signal qualitatively similar to the subject's tinnitus (e.g., hissing sound with a pressure of 65 decibels). The background acoustic signal is selected by sending a signal to the generator 206. Specifically, signals are sent to the complex waveform generator 312, the volume control 322, the sound mixer 324, and the amplifier 206 to select a wave signal having volume and amplitude associated with a hissing sound having a pressure of 65 decibels. The wave signal is converted to the selected background acoustic signal by the transducer 208 and exposed to the subject 202. Second, the control and recording circuit 300 selects a test acoustic signal by sending signals to the generator 206. Specifically, signals are sent to the complex waveform generator 312, the volume control 322, the sound mixer 324, and the amplifier 206 to select a wave signal having volume and amplitude associated with a hissing sound having a pressure of 75 decibels. The wave signal is converted to the selected test acoustic signal by the transducer 208 and exposed to the subject 202. Third, the control and recording circuit 300 sends a signal to the response sensing device 210 to begin monitoring the startle response of the subject 202. Forth, the control and recording circuit 300 selects a reflex stimulus (e.g., white noise having a pressure of 110 decibels) by sending signals to the generator 206. Particularly, signals are sent to the white noise generator 308, the volume control 322, the sound mixer 324, and the amplifier 206 to select a wave signal having volume, amplitude, and duration associated with a white noise stimulus having a pressure of 110 decibels. The wave signal is converted to the selected reflex stimulus sound pattern by the transducer 208 and exposed to the subject 202. The response sensing device 210 detects the subject's startle response. The four steps are repeated using a unique test acoustic signal in the second step to test the subject's pre-pulse inhibition for a second pre-pulse sound. Particularly, the test acoustic signal is selected to have hissing sound and a pressure of 80 decibels.

Figure 5A:
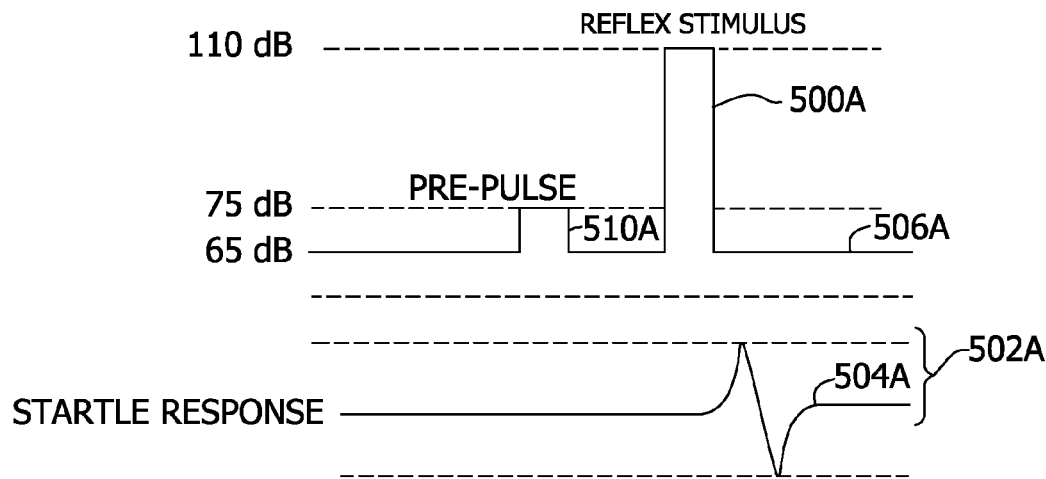
FIGS. 5A and 5B are graphs illustrating a startle response of a subject elicited using pre-pulse inhibition testing techniques for measuring the subject's tinnitus, according to an embodiment of the invention.
Figure 5B:
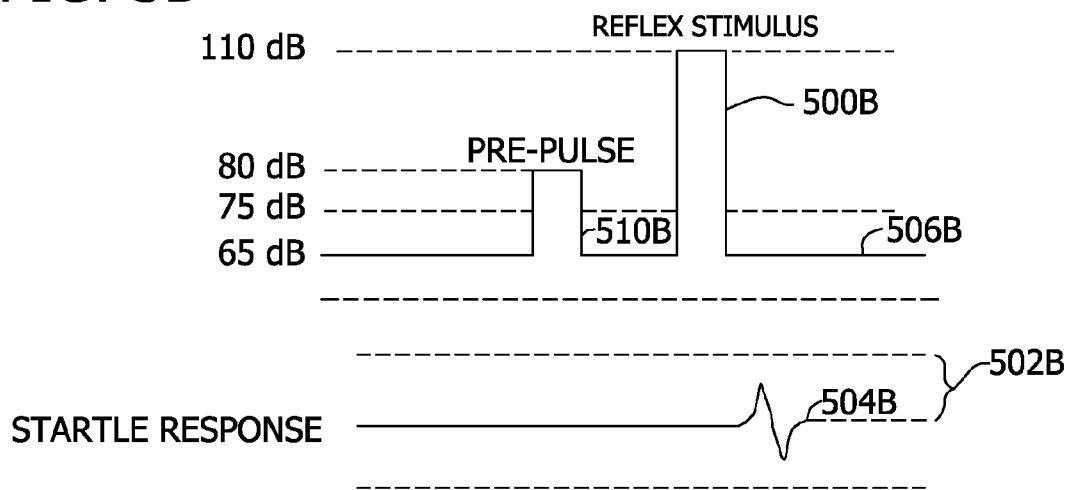
Figure 5C:
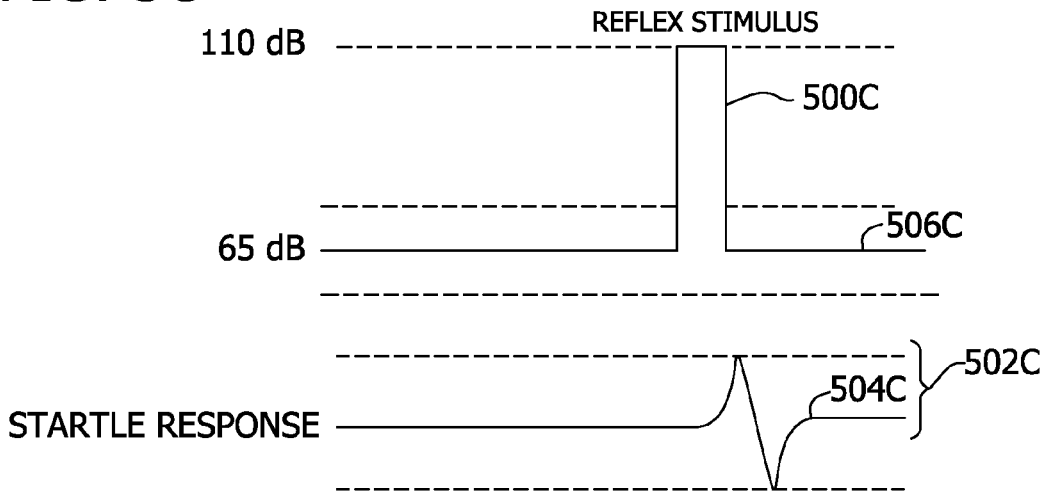
FIG. 5C is graph illustrating a startle response of a subject elicited by a reflex stimulus for measuring the subject's tinnitus, according to an embodiment of the invention.

FIGS. 5A and 5B illustrate the sound patterns exposed to the subject 202 and the subject's startle response. The sound patterns include the background acoustic signal 506, the test acoustic signal (e.g., the pre-pulse 510), and the reflex stimulus 500. The subject's startle response to the reflex stimulus 500A when preceded by the first test acoustic signal 510A has an amplitude 502A. The subject's startle response to the reflex stimulus 500B when preceded by the second test acoustic signal 510B has an amplitude 502B. The amplitudes 502A, 502B quantify the subject's acoustic startle reflex. Specifically, since the subject's acoustic startle reflex is inhibited where the subject 202 detects a pre-pulse, the amplitude of the subject's startle response will be less where the subject 202 detects a pre-pulse. Accordingly, the control and recording circuit 300 uses the amplitudes 502A, 502B to determine whether the subject 202 detected the pre-pulse 510 in the sound pattern 506. Referring to FIGS. 5A, 5B and 5C, in one embodiment, the control and recording circuit 300 determines whether the subject 202 detected the pre-pulse 510 in the sound pattern 506 by comparing (a) the amplitude 502A, 502B of the startle response 504A, 504B to a reflex stimulus 500 preceded by a pre-pulse 510A, 510B; and (b) the amplitude 502C of a startle response to a reflex stimulus 500C not preceded by a pre-pulse. The latter startle amplitude 502C can be obtained using an embodiment of the present invention or by any method or device known in the art and then communicated to the control and recording circuit 300. The control and recording circuit 300 determines that the subject detects the pre-pulse in the sound pattern 510 if the ratio of the amplitude 502A, 502B to the amplitude 402C is equal to one, and determines that the subject does not detect some portion of the pre-pulse in the sound pattern 510 if the ratio is less than one. In this scenario, although the background acoustic signal was selected to substantially match the subject's perceived noise (tinnitus), the subject 202 was unable to detect the presence of the first test acoustic signal (e.g., the pre-pulse 410), which was 10 dB greater than the background acoustic signal. Since the subject 202 was unable to detect the presence of the background acoustic signal 506A, the pre-pulse 510A did not inhibit the subject's acoustic startle reflex quantified by the amplitude 502A of the startle response. Thus, the subject 202 can not detect the hissing sound at 65 dB or at 75 dB, suggesting the subject may have severe tinnitus preventing him from detecting sounds in at least a 10 dB range.

According to an embodiment, the control and recording circuit 300 uses the subject's startle responses to multiple sound patterns to determine the severity of the subject's tinnitus. For example, the control and recording circuit 300 determines the range of sound patterns that are affected by the subject's tinnitus by comparing (a) the amplitude 502A of the startle response 504A to a reflex stimulus 500A preceded by a first test acoustic signal (pre-pulse) 510A; (b) the amplitude 502B of the startle response 504B to a reflex stimulus 500B preceded by a second acoustic signal (pre-pulse) 510B and (c) the amplitude 502C of a startle response to a reflex stimulus 500C not preceded by a pre-pulse. In this scenario, although the subject was unable to detect the first test acoustic signal 510A which was 10 dB greater than the background acoustic signal, the subject was able to detect the second test acoustic signal 510B which was 5 dB greater than the first test acoustic signal and 15 dB greater than the background acoustic signal. Since the subject 202 was able to detect the presence of the second test acoustic signal, the pre-pulse inhibited the subject's acoustic startle reflex quantified by the amplitude 502B of the startle response such that the ratio amplitude 502B to 502C was less than one. Thus, the subject has mild tinnitus which affects the subject's perception of a 10 dB range of hissing sound.

In one embodiment, the severity of the subject's tinnitus is qualitatively measured by exposing the subject to a plurality of pre-pulse sounds and measuring the subject's startle response for each of the plurality of pre-pulse sounds. The plurality of pre-pulse sounds have varying characteristics (e.g., volume, frequency, amplitude, speed, wavelength, and the like) affecting the acoustic qualities (e.g., tone, sound pressure, pattern) of the sounds. Each pre-pulse sound has one characteristic that differentiates it acoustically from each of the other pre-pulse sounds. The control and recording circuit 300 analyzes the amplitudes of each of the subject's startle responses to determine the pre-pulse sounds which can and can not be detected by the subject. The control and recording circuit 300 determines that the subject's tinnitus prevents the subject from detecting a particular acoustic characteristic where the subject can detect a first pre-pulse sound but can not detect second pre-pulse where the particular acoustic characteristic is the only acoustic difference between the first pre-pulse sound and the second pre-pulse sound. In one embodiment, the control and recording circuit 300 additionally determines that the degree to which the subject detects the pre-pulse sounds as a function of the ratio of the amplitudes of the subject's responses to a first pre-pulse and a second pre-pulse sound. By determining whether the subject's tinnitus partially or completely prevents the subject from detecting a plurality of acoustic characteristics, the control and recording circuit determines the particular effects of the subject's tinnitus on the subject. The identification of these particular effects is advantageous to treating and coping with tinnitus. For example, if a subject's tinnitus prevents the subject from hearing hissing and whooshing sounds at 75 dB, the subject will be unable to acoustically detect approaching traffic. Thus, the subject will need to take responsive measures to safely travel in traffic areas.

Figure 6:
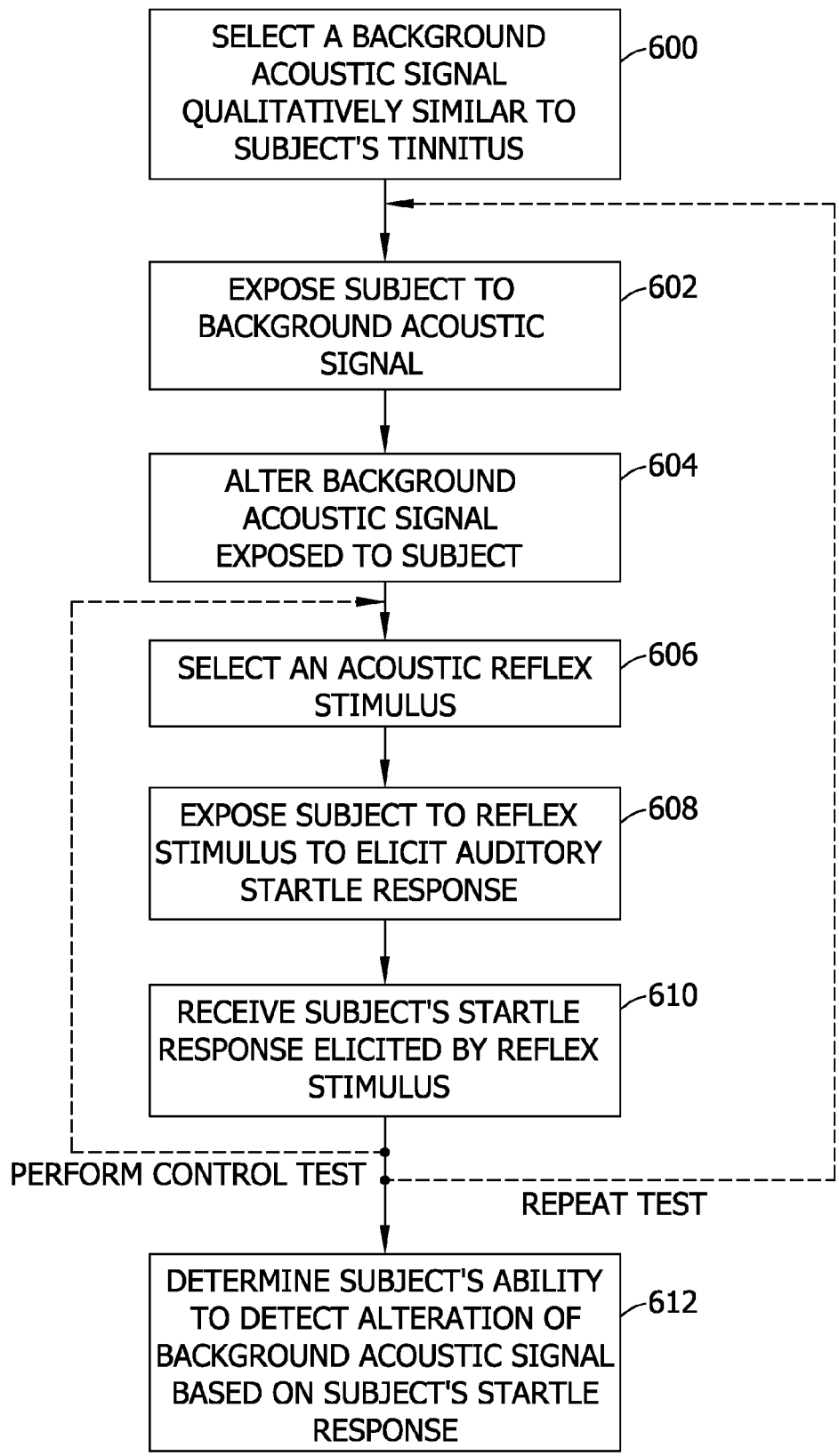
FIG. 6 is a flow diagram illustrating operations for objectively measuring a subject's tinnitus, according to an embodiment of the invention
Figure 7:
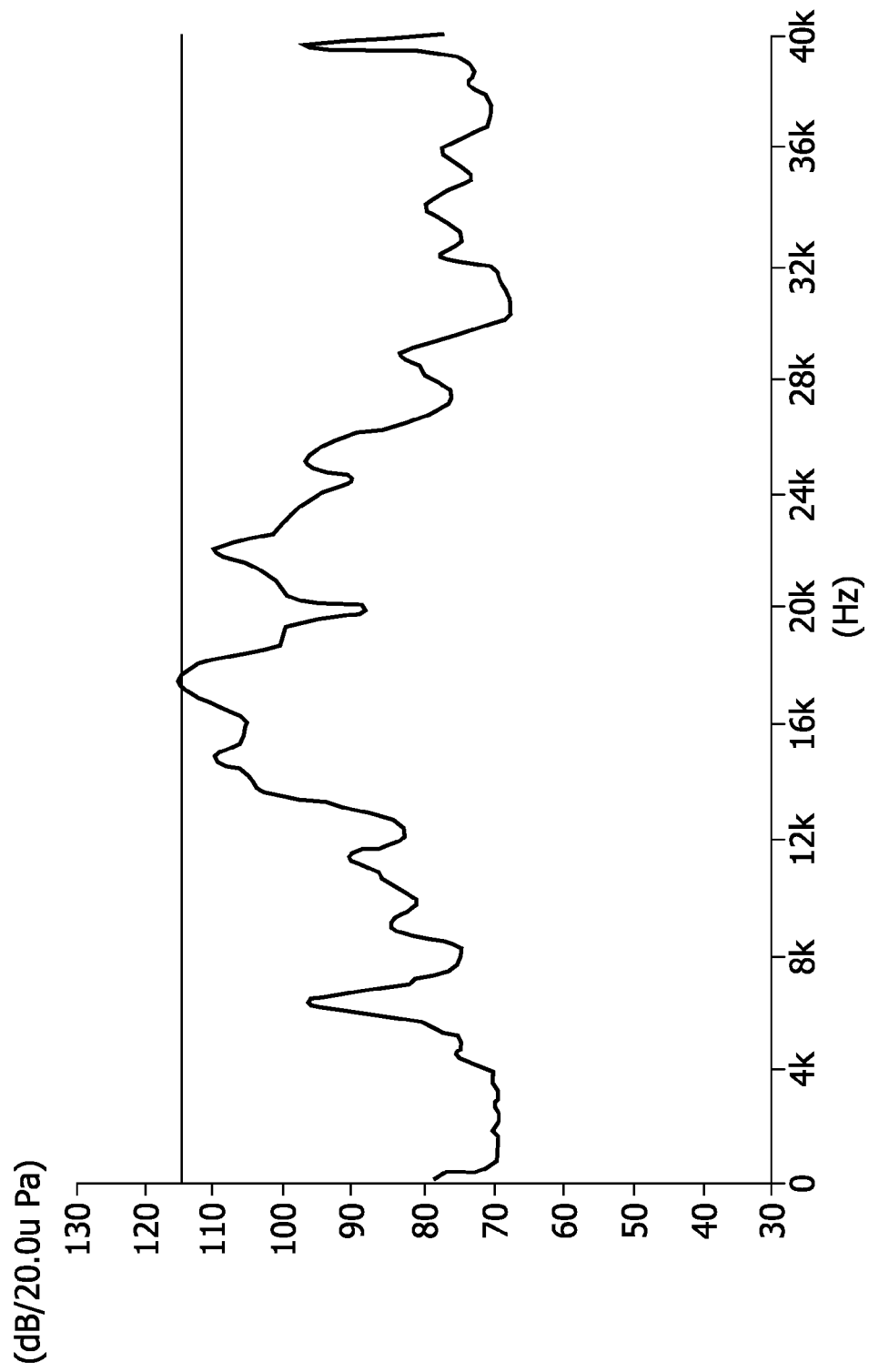
FIG. 7 is a graph illustrating the spectrum of a 16-kHz trauma signal used to produce tinnitus, according to an embodiment of the invention described in Appendices A and B.
Figure 8A:
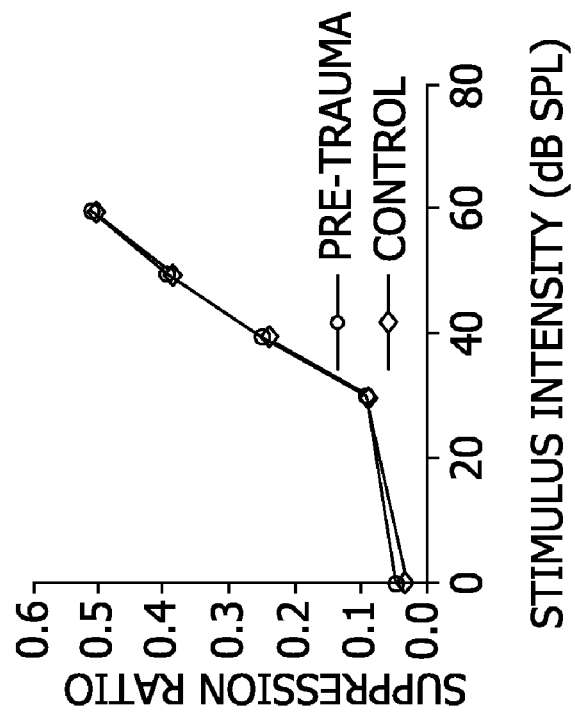
FIG. 8A is a graph illustrating psychophysical response of subjects exposed to a 10-kHz signal prior to exposure to a trauma signal, according to an embodiment of the invention described in Appendices A and B.
Figure 8B:
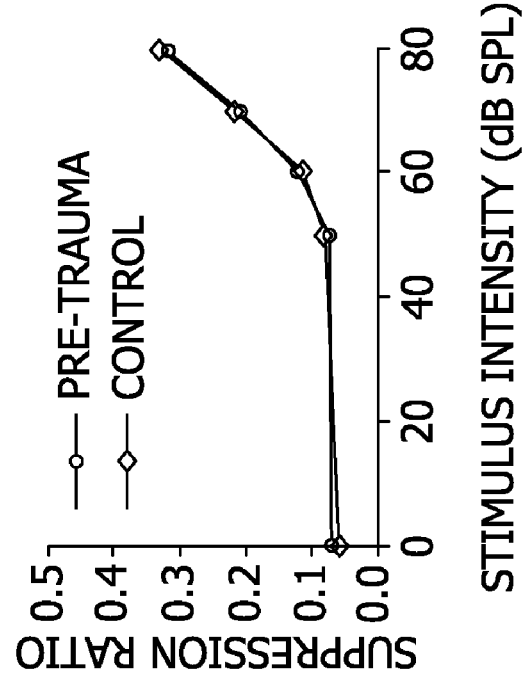
FIG. 8B is a graph illustrating psychophysical response of subjects exposed to a broadband noise signal prior to exposure to a trauma signal, according to an embodiment of the invention described in Appendices A and B.
Figure 8D:
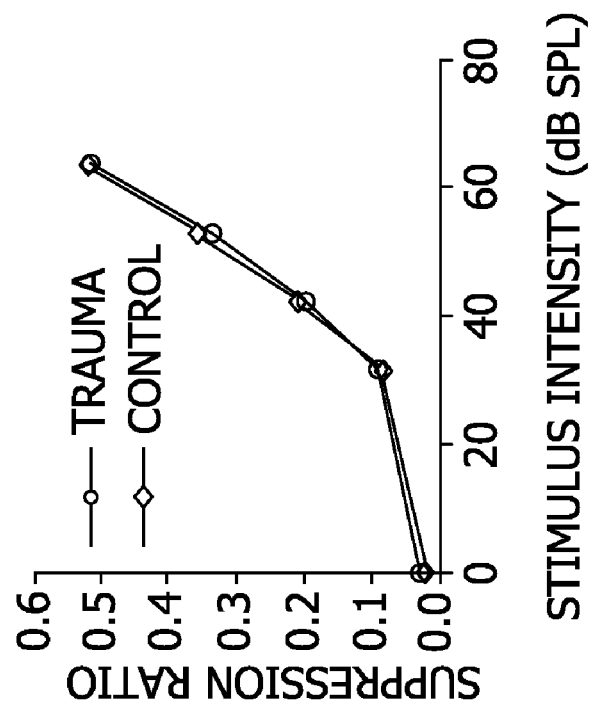
FIG. 8D is a graph illustrating psychophysical response of subjects exposed to a broadband noise signal two to four weeks subsequent to exposure to a trauma signal, according to an embodiment of the invention described in Appendices A and B.
Figure 8C:
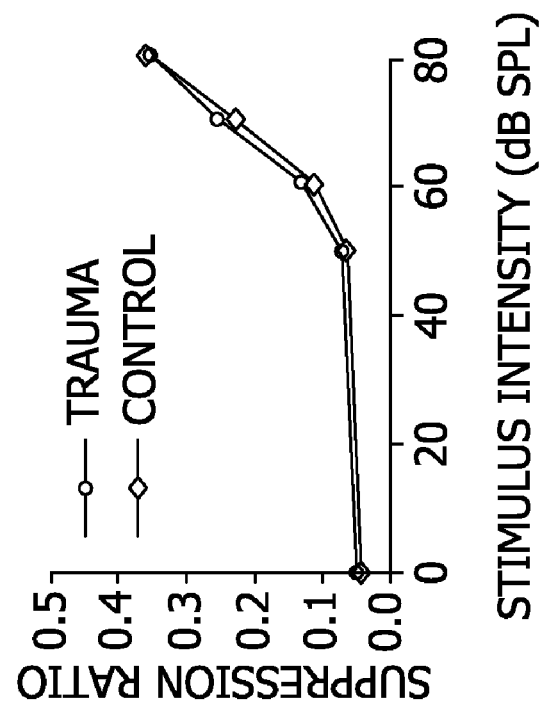
FIG. 8C is a graph illustrating psychophysical response of subjects exposed to a 10-kHz signal two to four weeks subsequent to exposure to a trauma signal, according to an embodiment of the invention described in Appendices A and B.
Figure 8F:
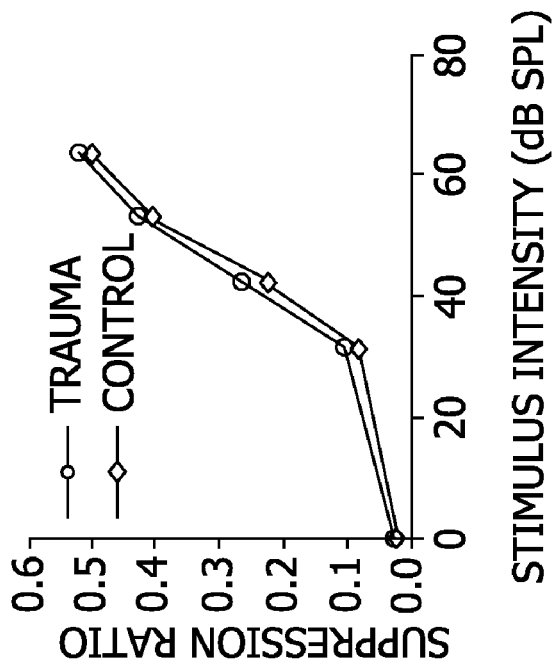
FIG. 8F is a graph illustrating psychophysical response of subjects exposed to a broadband noise signal eight to nine weeks subsequent to exposure to a trauma signal, according to an embodiment of the invention described in Appendices A and B.
Figure 8E:
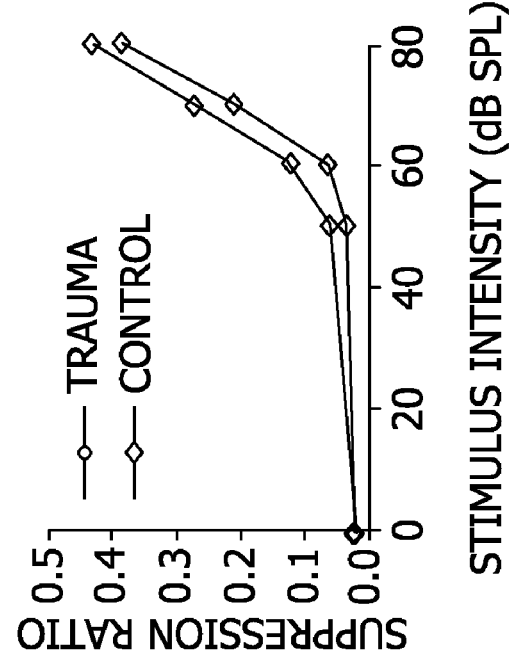
FIG. 8E is a graph illustrating psychophysical response of subjects exposed to a 10-kHz signal eight to nine weeks subsequent to exposure to a trauma signal, according to an embodiment of the invention described in Appendices A and B.

The flow diagram in FIG. 6, illustrates objectively measuring a subject's tinnitus according to one embodiment of the invention. At 600, a background acoustic signal qualitatively similar to the subject's tinnitus is selected. In one embodiment, the control and recording circuit 300 selects the background acoustic signal and the selecting of the background acoustic signal includes obtaining data from the subject 202, the testing administrator, and/or the storage memory 302 and basing the selection of the background acoustic signal on the obtained data.

In an embodiment, the selecting of the background acoustic signal at 600 further includes selecting a preliminary acoustic signal, exposing the preliminary acoustic signal to the subject, and obtaining a response from the subject indicating whether or not the preliminary sound matches the subject's tinnitus. For example, the control and recording device 300 displays, via the administrator interface 304, a list of available sounds (e.g., hissing, buzzing, pulsing) and/or characteristics (amplitude, duration, volume, frequency, speed) and the testing administrator indicates a particular acoustic signal. The preliminary sound pattern is exposed to the subject via a transducer 208 or any other sound producing device known in the art. The subject responds to the exposure via the subject interface 306 and may provide feedback information regarding the similarity of the preliminary sound to the subject's tinnitus (e.g., higher/lower frequency, higher/lower volume). If the subject 202 responds that the preliminary acoustic signal did not match the subject's tinnitus, a different preliminary acoustic signal is selected based on any responses/feedback from the subject 202. The process repeats until the subject 202 identifies a preliminary acoustic signal that is qualitatively similar to the subject's tinnitus. When the subject 202 identifies a preliminary acoustic signal that is substantially similar to the subject's tinnitus, that acoustic signal is selected as the background acoustic signal which is used to objectively measure the subject's tinnitus.

At 602, the subject 202 is aurally exposed to the selected background acoustic signal. A transducer 208 or any other sound producing device known in the art can be used.

At 604, the background acoustic signal is altered and the subject 202 is exposed to the sound resulting from the alteration. The alteration includes changing any characteristics of the sound wave associated with the background acoustic signal including but not limited to: amplitude, wavelength, duration, speed, frequency, volume. In addition the alteration includes removing the background acoustic signal from being exposed to the subject. In one embodiment, the background acoustic signal is altered to form a gap. A gap may be formed by removing or lowering the background acoustic signal for a period of time. In another embodiment, the background acoustic signal may be altered to include a pre-pulse. A pulse may be formed by interrupting the background acoustic signal with a test acoustic signal. The test acoustic signal has at least one acoustic characteristic that distinguishes it from the background acoustic signal.

At 606, a reflex stimulus is selected. In one embodiment, the control and recording circuit 300 selects a reflex stimulus and the selecting includes obtaining data from the subject 202, the testing administrator, and/or the storage memory 302 and basing the selecting of the reflex stimulus on the obtained data. The reflex stimulus can be any sound generally known in the art to elicit a startle response from a human or animal subject.

At 608, the subject is exposed to the reflex stimulus to elicit the subject's startle response. A transducer 208 or any other sound producing device known in the art can be used to expose the subject 202 to the stimulus.

At 610, the subject's startle response which was elicited by the reflex stimulus is received. In one embodiment, response sensing device 210 detects the subject's startle response, sends the detected startle response to the control and recording circuit 300 and the control and recording circuit receives the startle response. The startle response received includes quantifiable data describing the subject's startle response such as the amplitude of the detected startle response signal.

In one embodiment, after the subject's startle response is received, a control test is performed to gather data describing the subject's startle response to a reflex stimulus where the subject is not exposed to an alteration in background acoustic signal prior to the reflex stimulus. Returning to 606, a control reflex stimulus is selected. In one embodiment, the control and recording circuit 300 selects a control reflex stimulus and the selecting includes obtaining data from the subject 202, the testing administrator, and/or the storage memory 302 and basing the selecting of the control reflex stimulus on the obtained data. The control reflex stimulus can be any sound generally known in the art to elicit a startle response from a human or animal subject. In one embodiment, the control reflex stimulus is qualitatively similar to the reflex stimulus. Returning to 608, the subject is exposed to the control reflex stimulus to elicit the subject's control startle response. Returning to 610, the subject's control startle response which was elicited by the control reflex stimulus is received. In one embodiment, the response sensing device 210 detects the subject's control startle response, sends the detected control startle response to the control and recording circuit 300 and the control and recording circuit receives the control startle response. The control startle response received includes quantifiable data describing the subject's control startle response such as the amplitude of the detected control startle response signal.

In one embodiment, after the subject's startle response is received, the test including steps 602-610 may be repeated. For example, the test may be repeated using acoustic signals having different characteristics (e.g., different background signal, different alteration of background signal, different reflex stimulus) so that the resulting startle responses can be compared in order to measure the severity of the subject's tinnitus. In another example, the test may be repeated in order to verify or correct the resulting startle response to the reflex stimulus. Alternatively, the test may be repeated in order to receive the subject's startle response under different conditions (e.g., different physical testing conditions, during different phases of treatment).

At 612, the subject's ability to detect the alteration of the background acoustic signal is determined based on the subject's startle response. In one embodiment, the determination includes comparing (a) the amplitude of the startle response to a reflex stimulus preceded by an alteration; and (b) the amplitude of a control startle response to a control reflex stimulus. In one embodiment, the control and recording circuit 300 determines that the subject has not detected the alteration if the ratio of (a) to (b) is equal to one. In this scenario, the subject perceives a noise (i.e., tinnitus) substantially matching the background acoustic signal exposed at 602 so the subject was unable to detect the alteration of the background acoustic signal at 604. Since the subject was unable to detect the alteration, the alteration did not inhibit the subject's acoustic startle reflex quantified by the amplitude of the startle response received at 610. Thus, the subject experiences some form of tinnitus. The control and recording circuit 300 determines that the subject detects the alteration in the background acoustic signal if ratio of (a) to (b) is less than one. In this scenario, although the background acoustic signal was selected at 600 to substantially match the subject's perceived noise (tinnitus), the subject was able to detect the alteration of the background acoustic signal (e.g., the prepulse 410) at 604. Since the subject was able to detect the alteration of the background acoustic signal at 604, the alteration did not inhibit the subject's acoustic startle reflex quantified by the amplitude of the startle response received at 610. Thus, the subject does not have tinnitus according to the acoustic characteristics of the exposed signals. In another embodiment, amplitudes of various startle responses corresponding to various characteristics of acoustic signals are compared in order to measure the severity of the subject's tinnitus.

Embodiments of the present invention have several advantages over conventional subjective tinnitus testing, including accurately and reliably detecting and measuring tinnitus. Additionally, aspects of the present invention can be applied to both humans and animals because it does not rely on the subject's subjective response or previous behavioral training. Appendix A details an application of aspects of the present invention to objectively measure tinnitus in rat subjects. Before applying these aspects to objectively measure tinnitus in the rats, the rats were inflicted with tinnitus and tested to ensure the rat subjects indeed experienced tinnitus. Appendix B details the preparation of the rat subjects for use in the experiment of Appendix A. The subject matter of Appendix A and B was presented in Turner, Jeremy G., Thomas, Brozoski, Bauer, Carol A., Parrish, Jennifer L., Myers, Kristin, Hughes, Larry F., & Caspary, Donald M. (2006) "Gap Detection Deficits in Rats With Tinnitus: A Potential Novel Screening Tool" *Behavioral Neuroscience* 189-193. In addition to illustrating the accuracy and reliability of the present invention, the experimental data illustrates advantages of using the apparatus and methodology described herein to objectively measure tinnitus in animal subjects. The advantages include (a) food or water deprivation is not necessary; (b) no training, learning, memory, or motivational demands are placed on the animal; (c) the startle neural circuit is well known, and its modulation using background sounds has been studied extensively (Koch & Schnitzler, 1997; Swerdlow, Braff, & Geyer, 1999; Swerdlow, Geyer, & Braff, 2001); and (d) testing can be done quickly in a single 40 minute session, allowing rapid assessment of acute manipulations. (See Turner et al., "Gap Detection Deficits in Rats With Tinnitus: A Potential Novel Screening Tool" *Behavioral Neuroscience* 188).

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

APPENDIX A

Experiment: Gap Detection Deficits in Rats with Tinnitus: A Novel Screening Tool Part I: Experimental Hypothesis, Method, Gap Detection, Results, & Discussion A. Experiment Hypothesis We hypothesized that when the background sound in which the gap is embedded is qualitatively similar to an animal's tinnitus, poorer detection of the silent gap would occur. Data presented here confirm that rats with independent evidence of tinnitus at 10 kHz, compared with controls, demonstrate difficulty detecting a silent gap in a 10 kHz background sound.

B. Method

The rats used to conduct this experiment were obtained from Brozoski, Bauer and Myers and testing relating to the Brozoski, Bauer and Myers technique discussed in this experiment was performed by Brozoski, Bauer and Myers. The experimental protocol was approved by the Southern Illinois University School of Medicine Laboratory Animal Care and Use Committee.

Thirty-one young-adult male Long-Evans rats were used to conduct the experiment. All rats were obtained from Harlan (Indianapolis, Ind.) and were approximately 10 to 11 months old with a mean weight of 350 g at the time of gap detection testing. Rats were individually housed within a colony room maintained at 25° C. and with a 12-hr reversed light-dark-schedule.

Various statistical methods were used to analyze data gathered during the experiment. Particularly, the F-distribution and the t-distribution are used in this Appendix A and Appendix B to discuss the experimental data. The F-distribution is a statistical measure of the spread or scattering of members of two observed random samples as a test of whether the samples have the same variability. The F-distribution is obtained by taking the ratio of the chi-square distributions of the samples divided by the number of their degrees of freedom. The F-distribution is represented using the notation F(degrees of freedom of numerator, degrees of freedom of denominator) wherein a p-value represents the probability of samples having values which are not represented in the F-distribution. The t-distribution is a theoretical probability distribution. It is symmetrical, bell-shaped, and similar to the standard normal curve but includes a degrees of freedom parameter. The t-distribution is represented using notation t(degrees of freedom) wherein a p-value represents the probability of having values which are not represented in the t-distribution.

C. Gap Detection Testing

After determining that trauma rats displayed operant evidence of tinnitus in the 10 kHz range, we began gap detection testing for tinnitus. Testing was conducted using Hamilton-Kinder startle reflex hardware and software, customized for this application by the manufacturer (Hamilton-Kinder Behavioral Testing Systems, Powny, Calif.). Gap detection testing was conducted with background noise presented through a Pioneer speaker (Model A1365) located in the door wall and startle stimuli presented through a speaker located in the ceiling of the testing chamber, 15 cm above the animal's head. The floor of the chamber, attached to a piezo transducer, provided a measure of startle force applied to the floor. A clear polycarbonate animal holder, with holes cut for sound passage, was suspended above the floor, allowing the rat to freely turn around while minimizing excessive movement. An adjustable-height roof was set to a level that kept rats from rearing up, a behavior that adds variability to the startle response.

Background signals in the startle chamber consisted of BBN, or bandpass filtered noise centered at 10 kHz (9.5-10.5 kHz bandpass, 48 dB/octave roll off, Krohn-Hite Model 3988) or 16 kHz (15.5-16.5 kHz band-pass). The three test conditions were run sequentially, each lasting approximately 12 minutes. Rats remained in the chambers between tests. Test stimuli were calibrated at 60 dB SPL peak levels with a cloth model rat and a Bruel and Kjaer Pulse System with a 0.5-in. free-field microphone (Bruel & Kjaer Model 4191). Baseline noise levels in the test chamber (with background test noise turned off) were measured between 42 and 52 dB SPL in the 2-36 kHz range. The order of presentation for the three test conditions was counterbalanced across rats to control order effects. Other than the acoustic features of the background stimulus, the three consecutive 10-min test conditions were identical. Each test consisted of 24 trials presented with a 20-s variable intertrial interval. Each session began with a 2-min acclimation period followed by two trials consisting of an abrupt startle-eliciting noise burst (115 dB SPL, 20-ms duration), which served to habituate the startle response to a more stable baseline. Data from the two initial trials were not used in the detection analysis. The remainder of the session consisted of 10 additional startle-only trials pseudorandomly mixed with 12 gap trials. Gap trials were identical to startle-only trials, except for the inserted gap. Gaps always began 100-ms before the startle stimulus and were 50-ms in duration, and were shaped with a 0.1-ms rise/fall gate. Previous work showed that 50-ms gaps beginning 100 ms before a startle stimulus produced stable, asymptotic levels of gap-induced inhibition of the startle reflex in rats (Turner et al., 2005, Association for Research in Otolaryngology Abstract). Previous startle literature suggests that startle testing does not cause temporary or permanent threshold elevations in mice. (Turner & Willott, 1998). A pilot experiment using the present equipment and stimulus settings revealed no pre- to post-treatment testing ABR threshold shifts in Long-Evan rats, either immediately, $F(1, 14)=0.77$, $p=0.40$, or 1 week after startle testing, $F(1, 14)=0.32$, $p=0.58$.

D. Results

FIG. 8 depicts gap detection performance in tinnitus and control rats as a function of acoustic background. Tinnitus rats showed significantly worse gap detection when the gap was embedded in the 10 kHz background condition $F(1, 25)=4.91$, $p=0.036$. No significant impairments in gap detection between tinnitus and control animals were observed for either the 16 kHz background, $F(1, 25)=1.55$, $p=0.23$, or BBN background, $F(1, 25)=0.03$, $p=0.86$. Overall startle reflex magnitude (control trials only) was not significantly different between tinnitus and control rats overfill, $F(1, 25)$ 0.74, $p=0.40$, or in any of the three stimulus test conditions separately: 10 kHz, $F(1, 25)=0.32$ $p=0.57$, 16 kHz, $F(1, 25)=1.88$, $p=0.88$, or BBN, $F(1, 25)=0.12$, $p=0.73$. These results suggest that the deficits in 10 kHz gap detection in tinnitus rats are not simply an artificial by-product of altering the baseline startle reflex (denominator in gap detection ratio).

E. Discussion

Rats with prior independent evidence of tinnitus at 10 kHz exhibited significantly worse gap detection than controls when the gaps were embedded in a 10 kHz background. This finding lends validity to the present gap detection method for measuring tinnitus. No significant gap detection differences were found between tinnitus and control rats with either the 16 kHz or BBN backgrounds. These results support the hypothesis that an animal with tonal tinnitus will show impaired gap detection in an acoustic environment with features resembling its tinnitus.

The gap detection results suggest that rats with independent evidence of tinnitus in the 10 kHz region were deficient in detecting a silent, 50-ms duration gap in a 10 kHz background stimulus. The noise floor in the chamber was measured between 42 and 52 dB SPL in. the 2-36 kHz range, suggesting that the "silent" gap in the 60 dB SPL background noise might be better described as a partially filled gap, with a drop in the overall background noise by 8-18 dB SPL in the frequency range of the test stimulus (10 kHz, 16 kHz, or BBN). In essence, the gap was already partially filled with environmental noise, and internal ringing (i.e., tinnitus) served to further fill the gap in tinnitus rats.

APPENDIX B

Experiment: Gap Detection Deficits in Rats with Tinnitus: A Novel Screening Tool Part II: Prior Training and Reliability Testing, Results, & Discussion A. Prior Training and Reliability Testing i. Prior Training, Tinnitus Induction, and Testing with an Established Independent Method Prior to gap detection testing, rats were trained, acoustically traumatized, then tested for tinnitus using Bauer and Brozoski's methods (see Bauer et al., 1999; Bauer & Brozoski, 2001; Brozoski Bauer. & Caspary, 2002). The procedure was used to establish the presence of tinnitus at 10 kHz in the experimental rats and to enable a comparison with the present gap detection technique. Briefly, rats were behaviorally trained in individual operant-conditioning chambers to lever press for food when any acoustic stimulus was present and to suppress lever pressing during stimulus-off periods. A variety of background sounds were used during 1-min test periods in each hour-long session, including broadband noise (BBN) and different pure tones of variable intensity. When the rats failed to suppress lever pressing to a criterion in a stimulus-off period, they were given a 1-s, 0.5 mA footshock at the end of that silent period. The critical discrimination for the rats was to distinguish between the absence of sound (when an end-of-period footshock was contingent on behavior) and the presence of (any) sound (when footshock was never given).

The rats were then divided into two groups equally matched in terms of discrimination performance across all stimulus conditions. Half of them received a unilateral 16 kHz, octave-band noise exposure, and the other half served as controls. The rats were anesthetized with an intramuscular injection of ketamine HCL (50 mg/kg) and xylazine (9 mg/kg) mixture, placed in a modified stereotaxic head frame, and unilaterally (left ear) exposed to octave-band noise with a peak intensity of 116 dB sound pressure level (SPL) centered at 16 kHz (see FIG. 6) for 1-hr. (All sound intensities are reported as unweighted SPLs at 20 µPa.) Output from a high-frequency speaker (40-1398, Realistic, RadioShack, Fort. Worth, Tex.) was directed into the left ear using a 3-mm cone-shaped speculum that fit tightly into the external auditory canal. Such treatment had previously been shown to produce temporary threshold shifts and evidence of chronic tinnitus in rats (Bauer et al., 1999; Bauer & Brozoski, 2001). Posttrauma psychophysical testing resumed 1 week after noise exposure and continued periodically for over 2 months after trauma. Use of these procedures has shown that animals exposed to acoustic trauma routinely suppress lever pressing at a higher rate than controls during the 10 kHz (but not other) test condition. This is used as evidence that a 10 kHz tinnitus is present, serving to augment the response to the 10 kHz background.

ii. Auditory Brainstem Response (ABR) Testing

Hearing thresholds for clicks and tone bursts at 10, 16, 20, 24, and 32 kHz were estimated using ABR. ABR thresholds were obtained before and after trauma, as well as at the end of the experiment (Intelligent Hearing Systems high-frequency system, Miami, Fla.). Subdermal stainless steel recording electrodes were inserted posterior to each pinna, with a reference electrode located at dorsal cranial midline and a ground electrode located in a rear leg. ABR thresholds were obtained for clicks and tone bursts, 5 ms in duration, presented at a rate of 50/s. Tone bursts were gated using an exact Blackman envelope (2.5-ms rise/decay, 0-ms plateau). Evoked potentials were amplified (200×), filtered (100-3,000-Hz bandpass), and averaged over 1,024 sweeps.

iii. Earplug Control Testing

To determine the effects of unilateral threshold elevations on gap detection performance, we tested a group of 5 control (nontraumatized normal hearing) rats for gap detection with and without a foam earplug. Rats were first tested under normal conditions for gap detection, as described above. They were then removed from the test chamber, and a foam earplug was inserted unilaterally into their left external auditory canal and temporarily held in place using a drop of ethyl cyanoacrylate. The rats were then returned to the test chamber and retested for gap detection. Following the earplug gap detection session, the animals were anesthetized and ABR thresholds were obtained to determine hearing in the plugged ear. Unilateral ABRs were first done with the earplug in place and repeated after removing the earplug from the canal.

Figure 10:
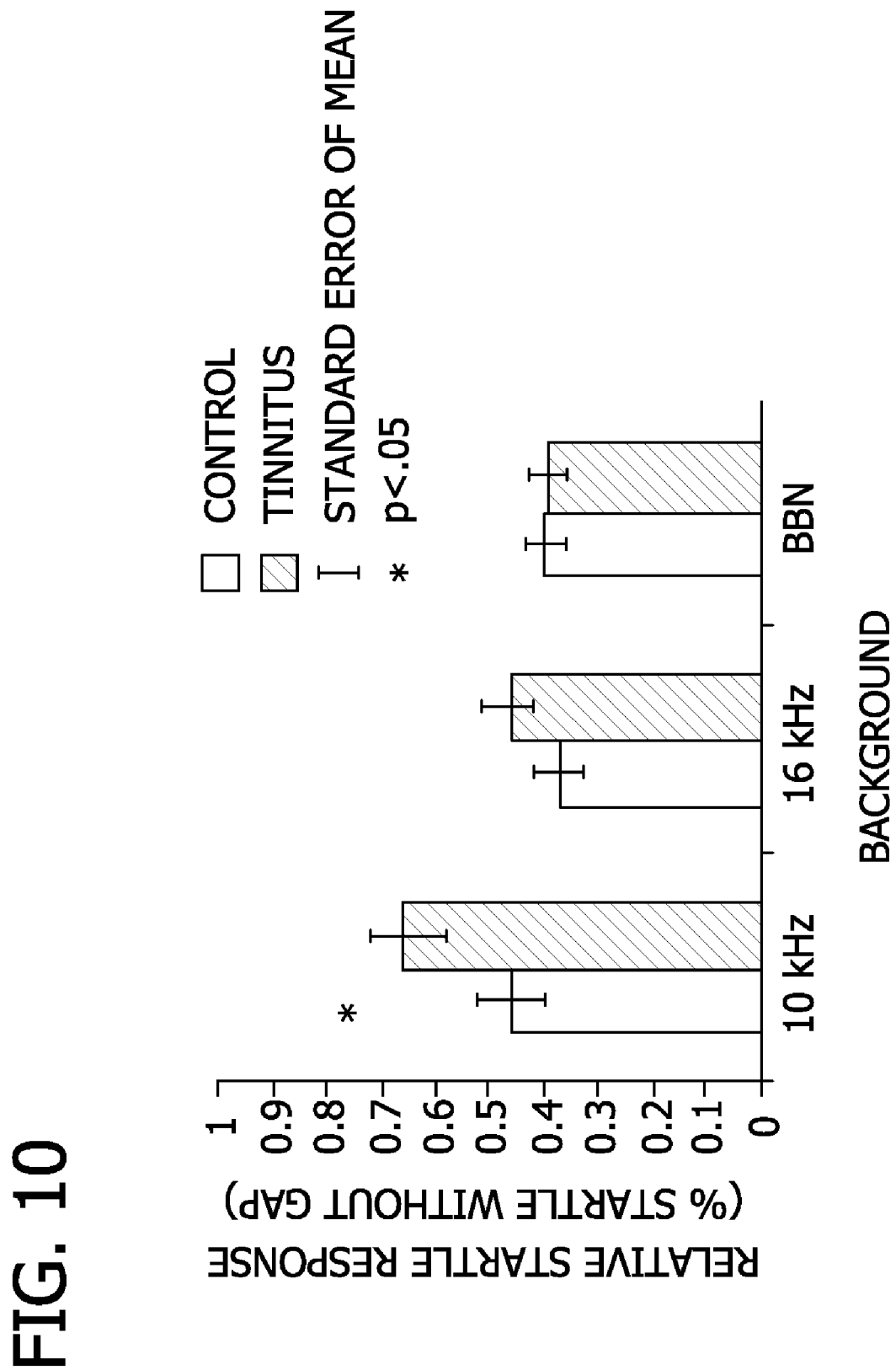
FIG. 10 is a graph illustrating gap detection performance as a function of acoustic background for tinnitus subjects and control subjects, according to an embodiment of the invention described in Appendices A and B.
Figure 11:
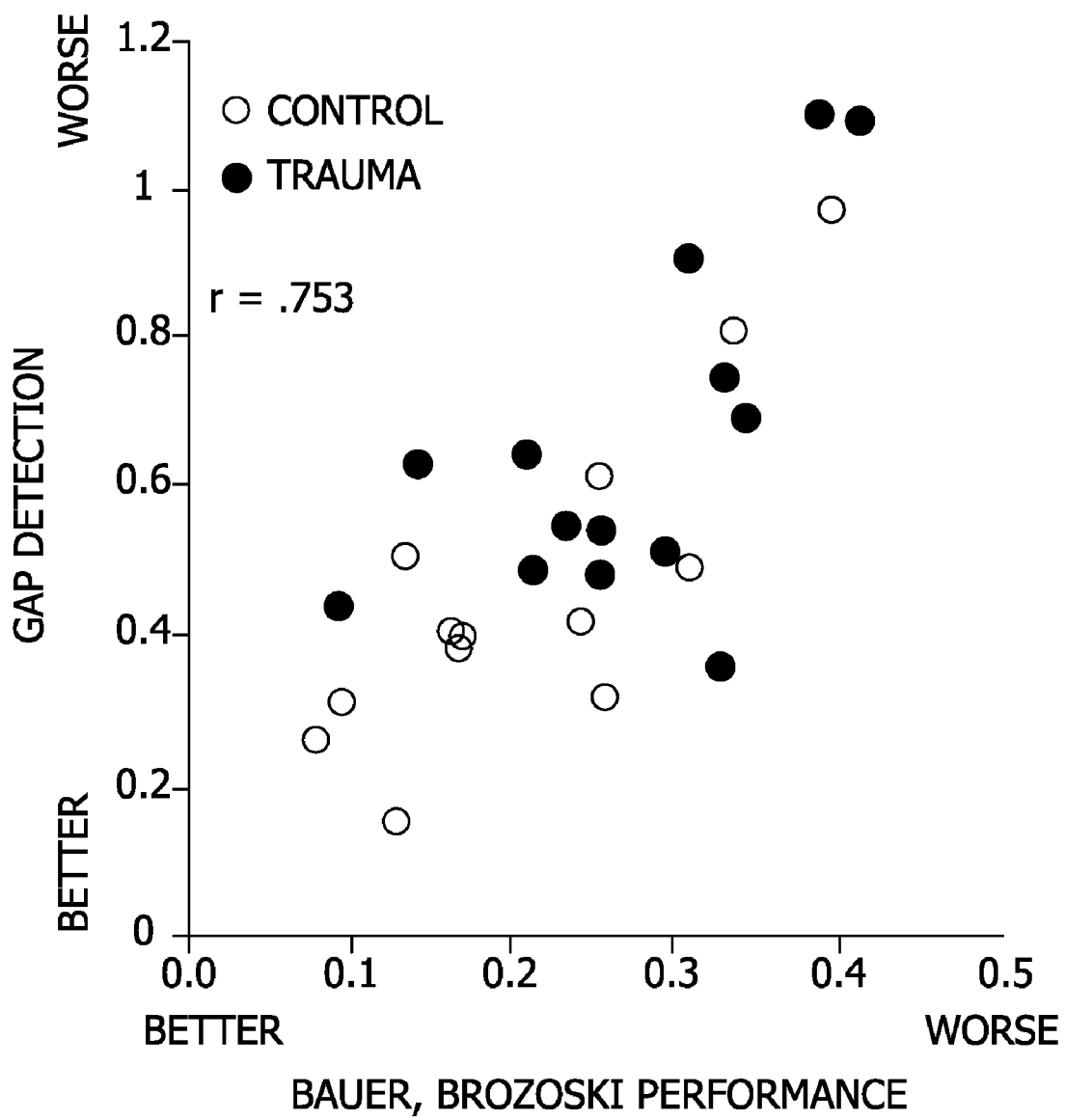
FIG. 11 is a scatterplot graph illustrating gap detection performance compared with performance on the Bauer and Brozoski operant test for tinnitus subjects and control subjects, according to an embodiment of the invention described in Appendices A and B.

B. Results i. Introduction and Verification of Tinnitus in Rats Prior to Gap Detection Testing Psychophysical testing using Bauer and Brozoski's method confirmed the presence of tinnitus in animals exposed to acoustic trauma. Trauma animals exhibited significant evidence of tinnitus at 8 to 9 weeks posttrauma by responding at a higher rate than controls during the 10 kHz test conditions, $t(25)=2.23$ $p=0.03$ (see FIGS. 7A-7F). No significant differences between trauma and control animals were present in the control BBN condition in any time period. FIG. 8 presents the corresponding ABR thresholds for tinnitus and control rats immediately before noise trauma, immediately after trauma, and approximately 4 months after trauma near the time of gap detection testing. Temporary threshold shifts were seen for clicks and all frequencies tested. However, at the time of behavioral gap detection testing 4 months later, ABR thresholds had recovered considerably and were not significantly different from pretest, levels at the suspected tinnitus frequency of 10 kHz. $t(13)=-1.10$, $p=0.29$.

ii. Comparing Gap Detection with an Operant Method of Tinnitus Determination Because each of the rats tested for gap detection was previously trained and tested for tinnitus using Bauer and Brozoski's operant method (Bauer et al, 1999; Bauer & Brozoskl, 2001), direct comparison between the two measures was possible. FIG. 10 compares the 10 kHz performance of each rat using the two methods. There was a significant positive correlation between the 10 kHz results obtained from the two methods, $r=0.753$, $F(1, 25)=32.78$, $p<0.01$. (The r represents a Pearson correlation coefficient and describes the relationship between two variables. Possible r values range from −1.0 to +1.0 with +1.0 suggesting a perfect, positive correlation. That is, as one measure goes up, the other measure goes up an equal amount. A significant positive correlation of 0.753 suggests the two values are highly related; that is, they seem to be measuring the same thing. In addition, neither method showed significant differences between tinnitus and control animals for either 16 kHz or BBN test conditions. It appears likely, therefore, that the independent operant-based and startle reflex-based methods are affected by the same phenomenon.

iii. Unilateral Hearing Loss Alone did not Significantly Affect Gap Detection Additional studies were undertaken to address whether gap detection deficits at 10 kHz in tinnitus rats could be explained by a unilateral hearing loss. In some rats, ABR threshold fully recovered to pretrauma control levels, whereas in other rats, partial threshold elevations remained. FIG. 11 depicts gap detection performance as a function of ABR threshold recovery in trauma animals. These data show that for the 5 rats with fully recovered ABR threshold, gap detection deficits were clearly present at 10 kHz, $t(16)=-1.76$, $p=0.049$. For the 6 rats whom ABR thresholds failed to fully recover, significant gap detection deficits were found not only at 10 kHz but also at 10 kHz exposure frequency, $t(9)=-1.95$, $p=0.04$.

Figure 12:
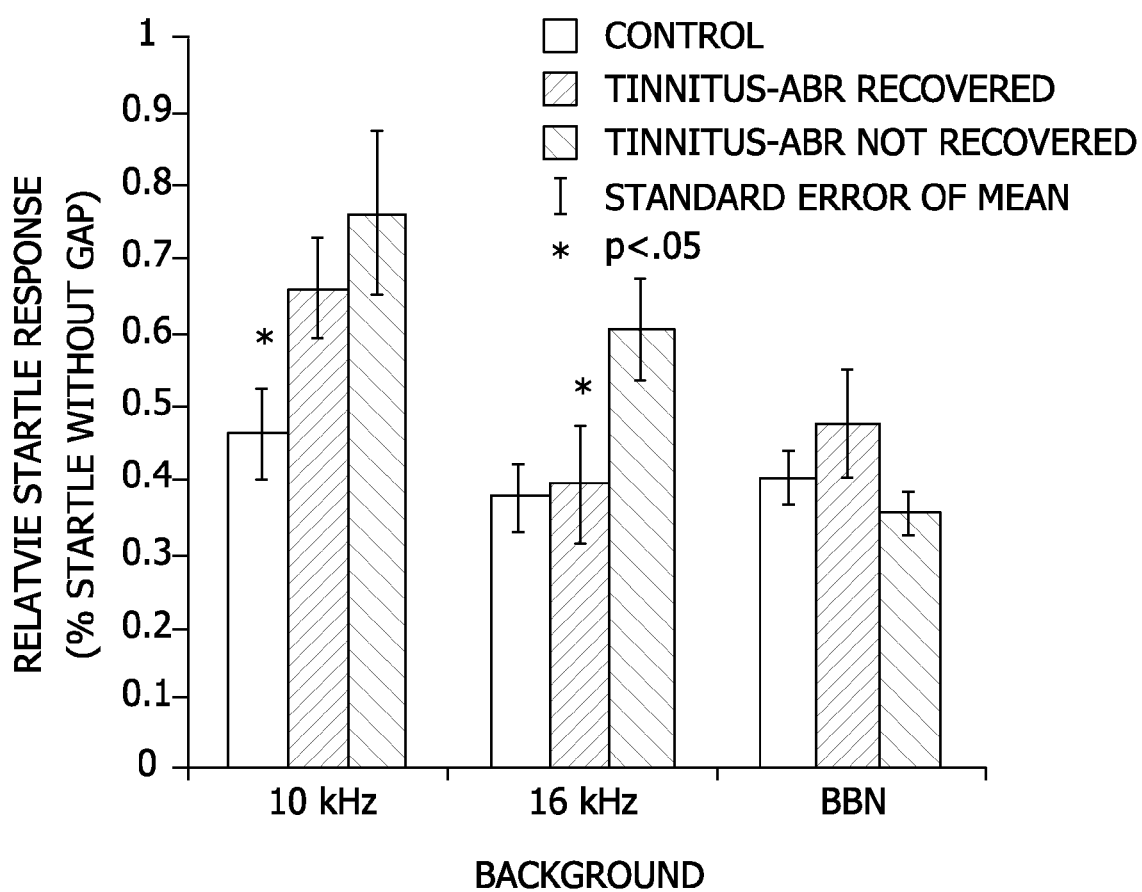
FIG. 12 is a graph illustrating gap detection performance as a function of recovered auditory brainstem response thresholds in subjects exposed to a trauma signal, according to an embodiment of the invention described in Appendices A and B.

Gap detection performance was also assessed at 10 kHz in 5 control rats with and without a unilateral foam earplug inserted to produce a temporary unilateral conductive hearing loss. ABR thresholds at 10 kHz were measured immediately after gap testing, first with the plug in place and again after removal. The ear plug produced a mean ipsilateral threshold elevation of 22 dB SPL (range: 5-35 dB), but, as depicted in FIG. 12, had no significant impact on 10 kHz gap detection performance. For purposes of comparison, note that tinnitus in rats displayed only a modest, non-significant threshold elevation of about 6 dB (see FIG. 3).

iv. Effects of Prior Training on Gap Detection

Figure 9:
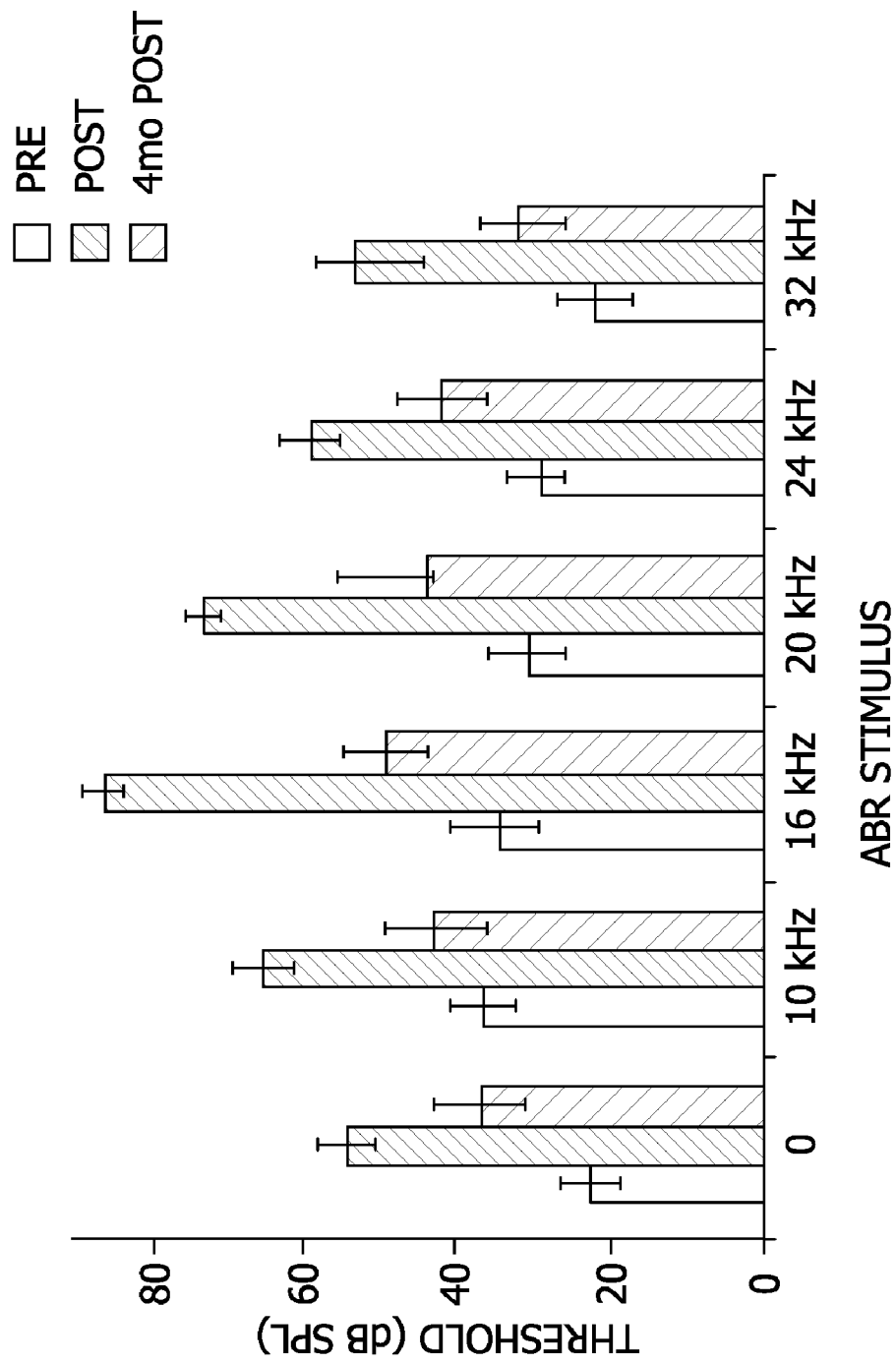
FIG. 9 is a graph illustrating auditory brainstem response thresholds of subjects immediately prior, immediately following, and 4 months following exposure to a trauma signal, according to an embodiment of the invention described in Appendices A and B.
Figure 13:
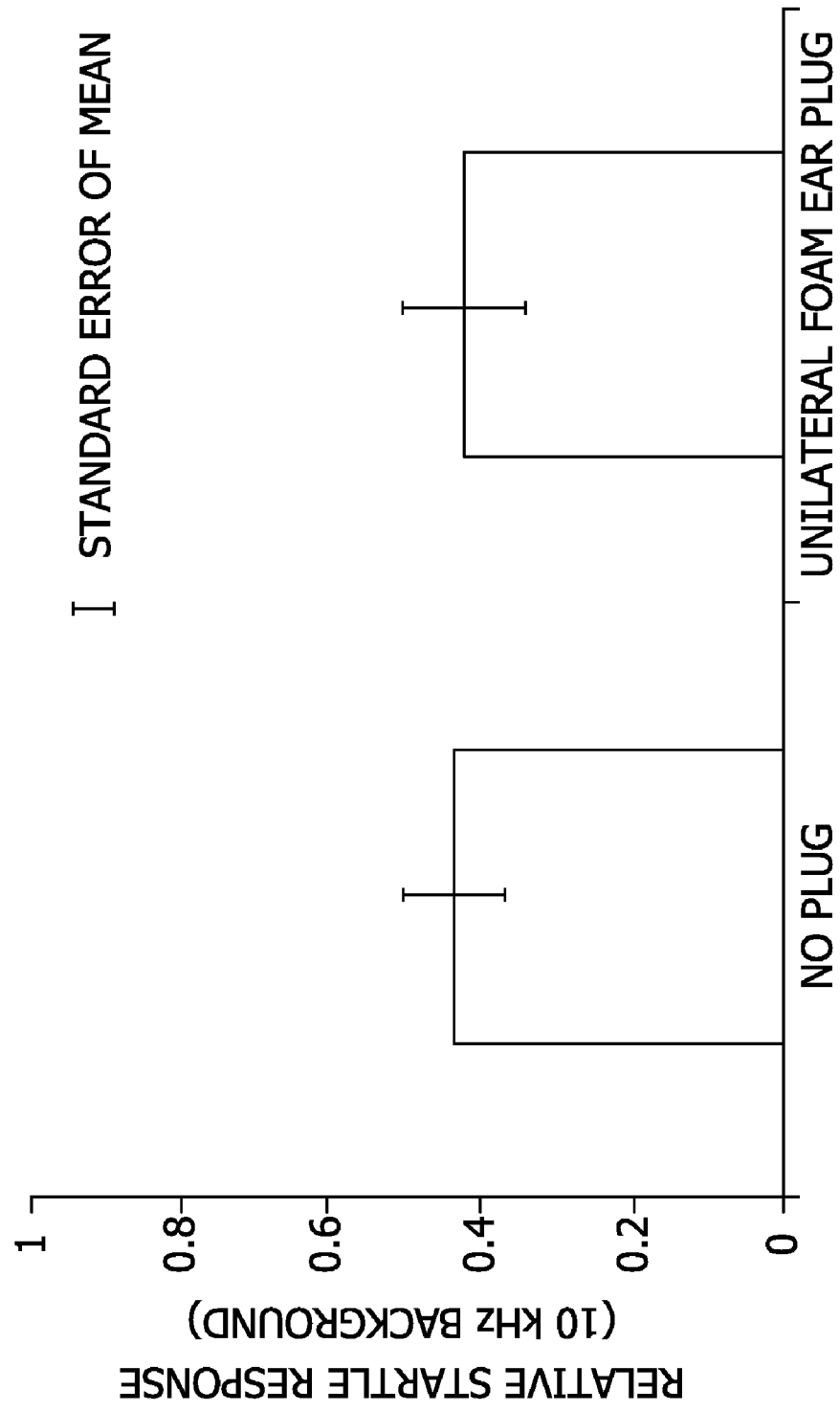
FIG. 13 is a graph illustrating gap detection performance in animals with an without a unilateral foam earplug, according to an embodiment of the invention described in Appendices A and B.

As all rats in the present study had been previously trained for several months to discriminate silence from BBN and pure gates, it was possible that the current gap detection findings were affected by the additional training (although control rats received the same training). To test this hypothesis, we conducted additional gap detection testing using four rats that had never been behaviorally trained. Two of the rats were exposed to the same trauma stimulus that produced tinnitus in the previously described behaviorally trained rats, and two served as controls. FIG. 13 shows the data from these four rats approximately 3 months after sound exposure. Similar to the data from trained rats (see FIG. 9), data from the exposed rats exhibited clear evidence of tinnitus at 10 kHz but did not differ from controls at 16 kHz.

C. Discussion

The selectivity of the findings (negative results at 16 kHz and BBN) suggest that worse gap detection at 10 kHz in tinnitus rats cannot easily be explained by either hearing loss or generally degraded performance. Maximum hearing loss was evident in trauma-exposed subjects at 16 kHz; at which no significant gap detection differences were obtained between trauma and control subjects. If hearing loss alone were to explain these results, the major difference between tinnitus and control rats would have been expected at 16 kHz, not at 10 kHz. In addition, the 10 kHz gap detection deficit was still evident when we compared control rats to tinnitus rats with fully recovered ABR thresholds at the time of testing. Hearing loss also seems an unlikely explanation, given the finding that a unilateral earplug producing a threshold shift of 2.2 dB, greater than that found in tinnitus rats, did not produce gap detection at 10 kHz. The earplug data further suggest that one fully functional ear is sufficient for perforating gap detection at control levels.

What is claimed is:

1. A method for objectively measuring tinnitus of a human or animal subject comprising:
   exposing the subject to a primary sound pattern, said primary sound pattern including a background acoustic signal qualitatively similar to the subject's tinnitus;
   exposing the subject to a reflex stimulus following exposure to the primary sound pattern, said reflex stimulus eliciting a reflex stimulus response by the subject; and
   measuring, with a response sensor, the reflex stimulus response by the subject, said reflex stimulus response being elicited by the exposure to the reflex stimulus to measure the subject's tinnitus.

2. The method of claim 1 further comprising:
   exposing the subject to a control sound pattern, said control sound pattern including the background acoustic signal qualitatively similar to the subject's tinnitus;
   exposing the subject to a control reflex stimulus for eliciting a control response by the subject, said control reflex stimulus being acoustically similar to the reflex stimulus;
   measuring the control response by the subject, said control response being elicited by said control reflex stimulus; and
   comparing the subject's response elicited by the reflex stimulus to the subject's control response elicited by the control reflex stimulus for determining the subject's ability to detect the background acoustic signal.

3. The method of claim 2 wherein the primary sound pattern comprises the background acoustic signal having a first duration and an audible gap in the background acoustic signal having a second duration, said second duration being shorter than said first duration, said audible gap including removing or lowering said background acoustic signal.

4. The method of claim 2 wherein the primary sound pattern comprises the background acoustic signal having a first duration and a test acoustic signal having a second duration, said second duration for exposing the test acoustic signal as a pulse and said second duration being shorter than said first duration.

5. The method of claim 4 further comprising:
   exposing the subject to a second sound pattern, said second sound pattern comprising the background acoustic signal having a first duration and a second test acoustic signal having a second duration, said second duration for exposing the test acoustic signal as a pulse and said second duration being shorter than said first duration, said second test acoustic signal being qualitatively different from the acoustic signal of the primary sound pattern;
   exposing the subject to the reflex stimulus following exposure to the second sound pattern, said reflex stimulus eliciting a second reflex stimulus response by the subject;
   measuring the second reflex stimulus response by the subject, said second reflex stimulus response being elicited by the exposure to the reflex stimulus following the second sound pattern; and
   comparing each of the subject's reflex stimulus responses for determining the severity of the subject's tinnitus.

6. The method of claim 5 wherein the test acoustic signal of the primary sound pattern is substantially prevented from being detected by the subject as a result of the subject's tinnitus and wherein the second test acoustic signal is detected by the subject.

7. The method of claim 1 further comprising selecting a preliminary acoustic signal for exposing to the subject in the primary sound pattern, and receiving feedback from the subject indicating whether or not the preliminary acoustic signal is qualitatively similar to the subject's tinnitus.

8. The method of claim 1 wherein the primary sound pattern is substantially prevented from being detected by the subject as a result of the subject's tinnitus.

9. The method of claim 1 wherein measuring the response from the subject elicited by the exposure to the reflex stimulus includes measuring brain wave activity of the subject associated with the response.

10. The method of claim 1 wherein measuring the response from the subject elicited by the exposure to the reflex stimulus includes measuring a startle response by the subject.

11. A device for objectively measuring an acoustic startle reflex of a human or animal subject comprising:
    a controller for selecting a primary sound pattern and selecting a reflex stimulus sound pattern to elicit an acoustic startle reflex by the subject, said selected primary sound pattern including bandpass filtered noise;
    a generator for generating signals associated with the sound patterns selected by the controller;
    a transducer for converting the generated signals to the selected sound patterns and exposing the selected sound patterns to the subject; and
    a response sensor for detecting the acoustic startle reflex by the subject to the selected reflex stimulus sound pattern, wherein the detected acoustic startle reflex from the subject to the selected reflex stimulus sound pattern indicates tinnitus.

12. The device of claim 11 wherein the generator includes an amplifier to set the amplitude and duration of the signals associated with the sound patterns selected by the controller.

13. The device of claim 11 wherein the generator includes a storage memory for storing data for generating signals associated with a plurality of primary sound patterns.

14. The device of claim 11 wherein the controller includes an interface for communicating with the subject and wherein the controller is configured for selecting the primary sound pattern based on said communication.

15. The device of claim 11 wherein the controller includes an interface for communicating with a test administrator and wherein the controller is configured for selecting the reflex stimulus sound pattern based on said communication.

16. The device of claim 11 wherein the controller includes an interface for communicating with a test administrator and wherein the controller is configured for selecting the primary sound pattern based on said communication.

17. The device of claim 11 wherein the response sensor detects changes in the subject's brain wave activity.

18. The device of claim 11 wherein the primary sound pattern includes a background acoustic signal, said background acoustic signal comprising the bandpass filtered noise.

19. A method implemented by one or more computing devices for objectively measuring tinnitus of a human or animal subject, said method comprising:
receiving, by the one or more computing devices from a response sensing device, a first startle response of the subject, said first startle response being elicited as a result of exposing the subject to a reflex stimulus;
receiving, by the one or more computing devices from the response sensing device, a second startle response of the subject, said second startle response being elicited as a result of sequentially exposing to the subject a primary sound pattern and the reflex stimulus, said primary sound pattern including an acoustic signal qualitatively similar to the subject's tinnitus; and
comparing by the one or more computing devices the first startle response of the subject to the second startle response of the subject to measure the subject's tinnitus.

20. The method of claim 19 further comprising:
receiving, by the one or more computing devices from the response sensing device, a third startle response of the subject, said third startle response being elicited as a result of sequentially exposing to the subject a second sound pattern and a second reflex stimulus, said second sound pattern including an acoustic signal qualitatively similar to the subject's tinnitus; and
comparing by the one or more computing devices the second startle response of the subject to the third startle response of the subject to qualitatively measure the subject's tinnitus.

21. The method of claim 20 wherein the primary sound pattern comprises the background acoustic signal having a first duration and an audible gap in the background acoustic signal having a second duration, said second duration being shorter than said first duration, said audible gap includes removing or lowering said background acoustic signal, and wherein said audible gap is substantially prevented from being detected by the subject as a result of the subject's tinnitus.

22. The method of claim 20 wherein the primary sound pattern comprises the background acoustic signal having a first duration and a test acoustic signal having a second duration, said second duration for exposing the test acoustic signal as a pulse and said second duration being shorter than said first duration, and wherein the test acoustic signal is substantially prevented from being detected by the subject as a result of the subject's tinnitus.

23. The method of claim 22 wherein the second sound pattern comprises the background acoustic signal having a first duration and a second test acoustic signal having a second duration, said second duration for exposing the second test acoustic signal as a pulse and said second duration being shorter than said first duration, said second acoustic signal being qualitatively different from the test acoustic signal of the primary sound pattern, and wherein the second test acoustic signal is detected by the subject.

* * * * *